(12) United States Patent
Hatakeyama et al.

(10) Patent No.: US 8,409,831 B2
(45) Date of Patent: Apr. 2, 2013

(54) METHOD FOR PRODUCING (1S,2R)-2-CHLORO-2-FLUOROCYCLOPROPANECARBOXYLIC ACID

(75) Inventors: Keisuke Hatakeyama, Toyonaka (JP); Takashi Miki, Toyonaka (JP); Norihiko Hirata, Suita (JP)

(73) Assignees: Sumitomo Chemical Company, Limited, Tokyo (JP); Daiichi Sankyo Company, Limited, Tokyo (JP)

( * ) Notice: Subject to any disclaimer, the term of this patent is extended or adjusted under 35 U.S.C. 154(b) by 144 days.

(21) Appl. No.: 13/003,499

(22) PCT Filed: Jul. 7, 2009

(86) PCT No.: PCT/JP2009/062388
§ 371 (c)(1),
(2), (4) Date: Jan. 10, 2011

(87) PCT Pub. No.: WO2010/005003
PCT Pub. Date: Jan. 14, 2010

(65) Prior Publication Data
US 2011/0117616 A1 May 19, 2011

(30) Foreign Application Priority Data
Jul. 11, 2008 (JP) .................. 2008-182066

(51) Int. Cl.
*C12P 7/40* (2006.01)
(52) U.S. Cl. ........................................ 435/136
(58) Field of Classification Search .................. None
See application file for complete search history.

(56) References Cited

U.S. PATENT DOCUMENTS

| 6,596,898 B2 | 7/2003 | Ebata et al. |
| 2001/0051750 A1 | 12/2001 | Ebata et al. |

FOREIGN PATENT DOCUMENTS

| EP | 0 858 992 A1 | 8/1998 |
| JP | 09-124556 A | 5/1997 |
| JP | 10-080298 A | 3/1998 |
| JP | 2001-000176 A | 1/2001 |
| JP | 2004-217608 A | 8/2004 |

OTHER PUBLICATIONS

Supplementary European Search Report dated Jan. 6, 2012 for EP Application No. 09794447.4, English Translation.

*Primary Examiner* — Tekchand Saidha
*Assistant Examiner* — Md. Younus Meah
(74) *Attorney, Agent, or Firm* — Sughrue Mion, PLLC

(57) ABSTRACT

The present invention provides a method for producing (1S,2R)-2-chloro-2-fluorocyclopropanecarboxylic acid with a high yield and high selectivity. Specifically, disclosed is a method for producing (1S,2R)-2-chloro-2-fluorocyclopropanecarboxylic acid, wherein (1S)-2-chloro-2-fluorocyclopropanecarboxylic acid ester is hydrolyzed using an esterase derived from *Burkholderia cepacia*.

9 Claims, No Drawings

METHOD FOR PRODUCING (1S,2R)-2-CHLORO-2-FLUOROCYCLOPROPANECARBOXYLIC ACID

TECHNICAL FIELD

The present invention relates to a method for producing (1S,2R)-2-chloro-2-fluorocyclopropanecarboxylic acid and a method for producing (1S,2S)-2-fluorocyclopropanecarboxylic acid.

BACKGROUND ART

One example of a method for producing (1S,2R)-2-chloro-2-fluorocyclopropanecarboxylic acid is to asymmetrically hydrolyze a mixture of four isomers of 2-chloro-2-fluorocyclopropanecarboxylic acid using an esterase (for example, as disclosed in Patent Literature (PTL) 1). However, the method disclosed in PTL 1 has a low yield and is problematic in terms of selectivity because the mixture of four isomers asymmetrically hydrolyzes.

CITATION LIST

Patent Literature

PTL 1: Japanese Unexamined Patent Publication No. 1998-80298

SUMMARY OF INVENTION

Technical Problem

Under such circumstances, the present inventors conducted intensive research to develop an industrially advantageous method for producing (1S,2R)-2-chloro-2-fluorocyclopropanecarboxylic acid and found that when (1S)-2-chloro-2-fluorocyclopropanecarboxylic acid ester is hydrolyzed using an enzyme that can selectively hydrolyze the (1R,2S)-2-chloro-2-fluorocyclopropanecarboxylic acid ester that is disclosed in PTL 1 mentioned above, (1S,2R)-2-chloro-2-fluorocyclopropanecarboxylic acid ester can be selectively hydrolyzed, and (1S,2R)-2-chloro-2-fluorocyclopropanecarboxylic acid can be produced with a high yield and high selectivity. The present invention has been accomplished based on this finding. The present inventors also found that (1S,2S)-2-fluorocyclopropanecarboxylic acid can be obtained by reducing the above-obtained (1S,2R)-2-chloro-2-fluorocyclopropanecarboxylic acid, and that the reduction can proceed with a higher yield when a reduction is conducted using an activated nickel-aluminum alloy.

Solution to Problem

The present invention provides Items 1-9 described below.

Item 1. A method for producing (1S,2R)-2-chloro-2-fluorocyclopropanecarboxylic acid comprising hydrolyzing a (1S)-2-chloro-2-fluorocyclopropanecarboxylic acid ester using an esterase derived from *Burkholderia cepacia*.

Item 2. The production method according to Item 1, wherein the method comprises reacting 1-chloro-1-fluoroethylene with diazoacetic acid ester in the presence of an asymmetric complex to obtain (1S)-2-chloro-2-fluorocyclopropanecarboxylic acid ester, and hydrolyzing the (1S)-2-chloro-2-fluorocyclopropanecarboxylic acid ester using an esterase derived from *Burkholderia cepacia*.

Item 3. The production method according to Item 2, wherein the asymmetric complex is an asymmetric copper complex obtained by contacting a copper compound with an optically active ligand.

Item 4. The production method according to Item 3, wherein the optically active ligand is an optically active bisoxazoline compound represented by Formula (1):

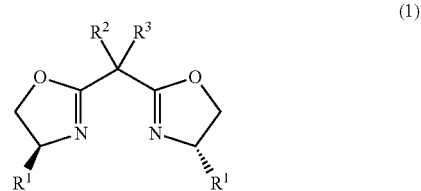

wherein $R^1$ represents a $C_{1-4}$ alkyl group, a phenyl group that may be substituted, an aralkyl group that may be substituted, 1-naphthyl group, or 2-naphthyl group; and $R^2$ and $R^3$ are the same or different and each represents a hydrogen atom or a $C_{1-3}$ alkyl group.

Item 5. The production method according to Item 3, wherein the optically active ligand is 2,2-bis[2-[(4S)-tert-butyloxazoline]]propane.

Item 6. The production method according to any one of Items 1 to 5, wherein the esterase derived from *Burkholderia cepacia* is an esterase having an amino acid sequence represented by SEQ ID NO: 1 or 2.

Item 7. The production method according to any one of Items 1 to 5, wherein the esterase derived from *Burkholderia cepacia* is an esterase having an amino acid sequence represented by SEQ ID NO: 1.

Item 8. A method for producing (1S,2S)-2-fluorocyclopropanecarboxylic acid comprising:
producing (1S,2R)-2-chloro-2-fluorocyclopropanecarboxylic acid by the production method according to any one of Items 1 to 7; and
reducing the (1S,2R)-2-chloro-2-fluorocyclopropanecarboxylic acid.

Item 9. The production method according to Item 8, wherein the reduction is conducted by allowing a base to react with a nickel-aluminum alloy in the presence of (1S,2R)-2-chloro-2-fluorocyclopropanecarboxylic acid.

Advantageous Effects of Invention

The present invention makes it possible to produce (1S,2R)-2-chloro-2-fluorocyclopropanecarboxylic acid with a high yield and sufficient selectivity. The present invention also makes it possible to produce (1S,2S)-2-fluorocyclopropanecarboxylic acid with a high yield by reducing the resulting (1S,2R)-2-chloro-2-fluorocyclopropanecarboxylic acid, thus is industrially advantageous.

DESCRIPTION OF EMBODIMENTS

The present invention is explained in detail below.

1. Method for producing (1S,2R)-2-chloro-2-fluorocyclopropanecarboxylic acid

1.1. (1S)-2-chloro-2-fluorocyclopropanecarboxylic acid ester

The process for producing the (1S)-2-chloro-2-fluorocyclopropanecarboxylic acid ester used in the present invention is explained below.

The (1S)-2-chloro-2-fluorocyclopropanecarboxylic acid ester can be produced by a method disclosed in Japanese Unexamined Patent Publication No. 2004-217608, Japanese Unexamined Patent Publication No. 1997-124556, or the like. Among those, the method of Japanese Unexamined Patent Publication No. 1997-124556 is preferable, wherein 1-chloro-1-fluoroethylene and diazoacetic acid ester are reacted in the presence of an asymmetric complex. A preferable example of the asymmetric complex is an asymmetric copper complex obtained by contacting a copper compound with an optically active ligand.

A monovalent or divalent copper compound can be used as the copper compound. Specific examples thereof include copper (I) acetate, copper (II) acetate, copper (I) trifluoroacetate, copper (II) trifluoroacetate, copper (I) naphthenate, copper (II) naphthenate, copper (I) octanoate, copper (II) octanoate, and like $C_{2-15}$ copper carboxylates; copper (I) chloride, copper (II) chloride, copper (I) bromide, copper (II) bromide, and like copper halides; copper (I) nitrate, copper (II) nitrate; and copper (I) methanesulfonate, copper (II) methanesulfonate, copper (I) trifluoromethanesulfonate, copper (II) trifluoromethanesulfonate, and like copper sulfonates. These copper compounds may be used singly or in combination. These copper compounds may be an anhydride or a hydrate. Among these, copper (II) trifluoromethanesulfonate and copper (I) trifluoromethanesulfonate are preferable. The copper (I) trifluoromethanesulfonate may be prepared, for example, using copper (II) acetate monohydrate, trifluoromethanesulfonic acid, and phenylhydrazine in a reaction system.

An example of an optically active ligand is an optically active bisoxazoline compound (hereunder referred to as optically active bisoxazoline (1)) represented by Formula (1) below:

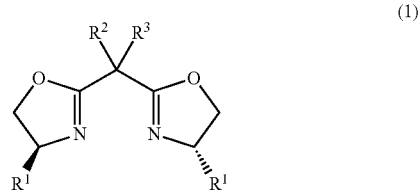

(1)

wherein $R^1$ represents a $C_{1-4}$ alkyl group, a phenyl group that may be substituted, an aralkyl group that may be substituted, 1-naphthyl group, or 2-naphthyl group; and $R^2$ and $R^3$ are the same or different and each represents a hydrogen atom or a $C_{1-3}$ alkyl group. Another example of an optically active ligand is a salicylaldimine compound (hereunder referred to as optically active salicylaldimine (2)) represented by Formula (2) below:

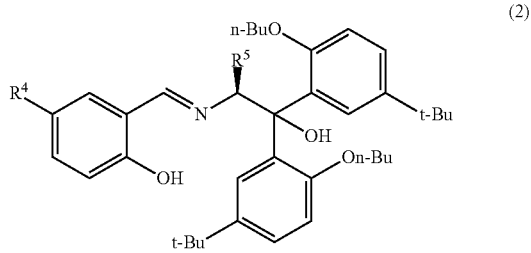

(2)

wherein $R^4$ represents a hydrogen atom or a nitro group, and $R^5$ represents a methyl group or a benzyl group. Among these, optically active bisoxazoline (1) is preferable.

Examples of the $C_{1-4}$ alkyl groups represented by $R^1$ in Formula (1) include methyl group, ethyl group, n-propyl group, isopropyl group, n-butyl group, isobutyl group, sec-butyl group, and tert-butyl group.

Examples of the groups optionally substituted on the phenyl group represented by $R^1$ include methyl group, ethyl group, n-propyl group, isopropyl group, n-butyl group, isobutyl group, sec-butyl group, tert-butyl group, n-pentyl group, n-hexyl group, cyclohexyl group, and like $C_{1-6}$ alkyl groups; and methoxy group, ethoxy group, n-propoxy group, isopropoxy group, n-butoxy group, isobutoxy group, sec-butoxy group, tert-butoxy group, n-pentyloxy group, n-hexyloxy group, cyclohexyloxy group, and like $C_{1-6}$ alkoxy groups. Examples of the phenyl groups substituted with such groups include 3-methylphenyl group, 4-methylphenyl group, 2-methoxyphenyl group, 3-methoxyphenyl group, and 4-methoxyphenyl group.

Examples of the aralkyl groups that may be substituted represented by $R^1$ include those composed of the optionally substituted phenyl groups described above, 1-naphthyl group or 2-naphthyl group, and the aforementioned $C_{1-6}$ alkyl groups. Specific examples thereof include benzyl group, 2-methylbenzyl group, 3-methylbenzyl group, 4-methylbenzyl group, 2-methoxybenzyl group, 3-methoxybenzyl group, 4-methoxybenzyl group, 1-naphthylmethyl group, and 2-naphthylmethyl group.

Preferable examples of $R^1$ include methyl group, isopropyl group, tert-butyl group, phenyl group, and benzyl group. Among these, tert-butyl group is particularly preferable.

Examples of the $C_{1-3}$ alkyl groups represented by $R^2$ and $R^3$ include methyl group, ethyl group, n-propyl group, and isopropyl group. It is preferable that $R^2$ and $R^3$ are both hydrogen atoms, both methyl groups, or both ethyl groups. It is particularly preferable that $R^2$ and $R^3$ are both methyl groups.

Specific examples of such optically active bisoxazolines (1) include bis[2-[(4S)-isopropyloxazoline]]methane, bis[2-[(4S)-tert-butyloxazoline]]methane, bis[2-[(4S)-phenyloxazoline]]methane, bis[2-[(4S)-benzyloxazoline]]methane, bis[2-[(4S)-(2-methoxyphenyl)oxazoline]]methane, bis[2-[(4S)-(4-methoxyphenyl)oxazoline]]methane, bis[2-[(4S)-(4-trifluoromethylphenyl)oxazoline]]methane, bis[2-[(4S)-(naphthalen-1-yl)oxazoline]]methane, bis[2-[(4S)-(naphthalen-2-yl)oxazoline]]methane, 2,2-bis[2-[(4S)-isopropyloxazoline]]propane, 2,2-bis[2-[(4S)-tert-butyloxazoline]]propane, 2,2-bis[2-[(4S)-phenyloxazoline]]propane, 2,2-bis[2-[(4S)-benzyloxazoline]]propane, 2,2-bis[2-[(4S)-(2-methoxyphenyl)oxazoline]]propane, 2,2-bis[2-[(4S)-(4-methoxyphenyl)oxazoline]]propane, 2,2-bis[2-[(4S)-(4-trifluoromethylphenyl)oxazoline]]propane, 2,2-bis[2-[(4S)-(naphthalen-1-yl)oxazoline]]propane, and 2,2-bis[2-[(4S)-(naphthalen-2-yl)oxazoline]]propane. Among these, 2,2-bis[2-[(4S)-tert-butyloxazoline]]propane is preferable.

The optically active bisoxazoline compound (1) may be a commercially available one or may be prepared by any known method (for example, the method disclosed in Japanese Unexamined Patent Publication No. 2006-45194).

In Formula (2), $R^4$ represents a hydrogen atom or a nitro group, and a nitro group is preferable.

Examples of optically active salicylaldimine (2) include [(S)-N-salicylidene-2-amino-1,1-di(5-tert-butyl-2-n-butoxyphenyl)-1-propanol]; [(S)-N-salicylidene-2-amino-1,1-di(5-tert-butyl-2-n-butoxyphenyl)-3-phenyl-1-propanol]; [(S)-N-(5-nitrosalicylidene)-2-amino-1,1-di(5-tert-butyl-2-n-butoxyphenyl)-1-propanol]; and [(S)-N-(5-nitrosalicylidene)-2-amino-1,1-di(5-tert-butyl-2-n-butoxyphenyl)-3-phenyl-1-propanol].

The optically active salicylaldimine (2) may be prepared by any known method (for example, the method disclosed in Japanese Unexamined Patent Publication No. 2001-2789853).

Here, commercially available 1-chloro-1-fluoroethylene may be used or the 1-chloro-1-fluoroethylene may be prepared by any known method.

Examples of diazoacetic acid esters include methyl diazoacetate, ethyl diazoacetate, n-propyl diazoacetate, isopropy diazoacetate, n-butyl diazoacetate, isobutyl diazoacetate, sec-butyl diazoacetate, tert-butyl diazoacetate, n-pentyl diazoacetate, n-hexyl diazoacetate, cyclohexyl diazoacetate and like $C_{1-6}$ alkyl esters. Among these, methyl diazoacetate, ethyl diazoacetate and n-propyl diazoacetate are preferable, and ethyl diazoacetate is particularly preferable.

The production method for diazoacetic acid ester is not limited and a known method, for example, that disclosed in Organic Synthesis Collective Volume 3, page 392, may be employed.

The amount of 1-chloro-1-fluoroethylene is generally 0.5 to 50 times by mol, preferably 1 to 10 times by mol, and more preferably 1.5 to 5 times by mol relative to the amount of the diazoacetic acid ester.

The amount of copper compound is generally 0.0001 to 1 time by mol, preferably 0.0005 to 0.1 times by mol, and more preferably 0.001 to 0.02 times by mol relative to the amount of the diazoacetic acid ester.

The amount of optically active ligand is generally 0.5 to 5 times by mol, preferably 0.5 to 3 times by mol, and more preferably 0.7 to 1.5 times by mol relative to the amount of the copper compound.

The reaction between 1-chloro-1-fluoroethylene and diazoacetic acid ester is generally conducted in the presence of a reaction solvent. Examples of usable reaction solvents include dichloromethane, dichloroethane, chloroform, n-butyl chloride, carbon tetrachloride, ortho-dichlorobenzene, trifluorotoluene and like halogenated hydrocarbon solvents; n-hexane, n-heptane, cyclohexane and like aliphatic hydrocarbon solvents; benzene, toluene, xylene and like aromatic hydrocarbon solvents; methyl acetate, ethyl acetate, n-propyl acetate, n-butyl acetate, n-pentyl acetate and like ester solvents; and tert-butyl methyl ether, tetrahydrofuran and like ethereal solvents. Among these, halogenated hydrocarbon solvents and aliphatic hydrocarbon solvents are preferable and ortho-dichlorobenzene, trifluorotoluene, and n-heptane are particularly preferable. These reaction solvents may be used singly or in a combination of two or more.

The amount of reaction solvent is not limited and it falls within the range of generally 100 times by weight or less, preferably 0.1 to 10 times by weight, and more preferably 0.5 to 3 times by weight relative to the amount of the diazoacetic acid ester.

The reaction temperature falls within the range of generally −78 to 50° C., preferably −30 to 30° C., and more preferably −10 to 20° C.

The reaction is generally carried out by mixing a copper compound and an optically active ligand, adding 1-chloro-1-fluoroethylene thereto, and adding diazoacetic acid ester to the mixture. Here, the addition of the diazoacetic acid ester is carried out generally over 1 to 50 hours, and preferably over 2 to 30 hours.

The reaction may be carried out under atmospheric pressure, but is preferably conducted under pressure using an autoclave or like pressure-resistant container. The proceeding of the reaction can be monitored by thin layer chromatography, gas chromatography, high-performance liquid chromatography or a like commonly used analytic technique.

The reaction mixture after the completion of the reaction contains (1S)-2-chloro-2-fluorocyclopropanecarboxylic acid ester, and the resulting reaction mixture may be supplied to the enzymatic hydrolysis of the present invention without further processing. However, (1S)-2-chloro-2-fluorocyclopropanecarboxylic acid ester is generally isolated from the reaction mixture by conducting washing, concentration or like standard post-processing before being supplied to the enzymatic hydrolysis of the present invention. Alternatively, the isolated (1S)-2-chloro-2-fluorocyclopropanecarboxylic acid ester may be supplied to the enzymatic hydrolysis of the present invention after being further purified by an ordinary purification treatment such as distillation or column chromatography.

Examples of (1S)-2-chloro-2-fluorocyclopropanecarboxylic acid esters thus obtained include (1S)-2-chloro-2-fluorocyclopropanecarboxylic acid methyl ester, (1S)-2-chloro-2-fluorocyclopropanecarboxylic acid ethyl ester, (1S)-2-chloro-2-fluorocyclopropanecarboxylic acid n-propyl ester, (1S)-2-chloro-2-fluorocyclopropanecarboxylic acid isopropyl ester, (1S)-2-chloro-2-fluorocyclopropanecarboxylic acid n-butyl ester, (1S)-2-chloro-2-fluorocyclopropanecarboxylic acid isobutyl ester, (1S)-2-chloro-2-fluorocyclopropanecarboxylic acid sec-butyl ester, (1S)-2-chloro-2-fluorocyclopropanecarboxylic acid tert-butyl ester, (1S)-2-chloro-2-fluorocyclopropanecarboxylic acid n-pentyl ester, (1S)-2-chloro-2-fluorocyclopropanecarboxylic acid n-hexyl ester, and (1S)-2-chloro-2-fluorocyclopropanecarboxylic acid cyclohexyl ester. Among these, (1S)-2-chloro-2-fluorocyclopropanecarboxylic acid methyl ester, (1S)-2-chloro-2-fluorocyclopropanecarboxylic acid ethyl ester and (1S)-2-chloro-2-fluorocyclopropanecarboxylic acid n-propyl ester are preferable, and (1S)-2-chloro-2-fluorocyclopropanecarboxylic acid ethyl ester is particularly preferable.

1.2. Hydrolysis of (1S)-2-chloro-2-fluorocyclopropanecarboxylic acid ester

A method for producing (1S,2R)-2-chloro-2-fluorocyclopropanecarboxylic acid, wherein the (1S)-2-chloro-2-fluorocyclopropanecarboxylic acid ester obtained above is hydrolyzed using an esterase derived from *Burkholderia cepacia* is explained below (in this specification, this method may be referred to as "the enzymatic hydrolysis of the present invention").

The esterase derived from *Burkholderia cepacia* (hereunder referred to as the enzyme of the present invention) may be one that is commercially available and may be prepared by any known method. As the enzyme of the present invention, an esterase having an amino acid sequence represented by SEQ ID NO: 1 or 2 is preferable and an esterase having an amino acid sequence represented by SEQ ID NO: 1 is more preferable.

An esterase having an amino acid sequence represented by SEQ ID NO: 1 can be prepared according to the method disclosed in the publication of Japanese Patent No. 3410128. More specifically, the lipase derived from *Pseudomonas cepacia* A-0727 (FERN-P No. 13272) in the publication of Japanese Patent No. 3410128 corresponds thereto. An esterase having an amino acid sequence represented by SEQ ID NO: 2 can be prepared by the method disclosed in the publication of Japanese Patent No. 3079276. The lipase derived from *Pseudomonas cepacia* M-12-33 (FERN-P No.9871) corresponds thereto. *Pseudomonas cepacia* disclosed in these publications is an old name for *Burkholderia cepacia*. The esterase having an amino acid sequence represented by SEQ ID NO: 1 and the esterase having an amino acid sequence represented by SEQ ID NO: 2, respectively, are commercially available from Amano Enzyme Inc. under the trade names of "lipase AH" and "lipase PS".

The enzyme of the present invention is known to have an ability to selectively hydrolyze (1R,2S)-2-chloro-2-fluorocyclopropanecarboxylic acid ester. When (1S)-2-chloro-2-fluorocyclopropanecarboxylic acid ester is hydrolyzed using the enzyme of the present invention having such an ability, (1S,2R)-2-chloro-2-fluorocyclopropanecarboxylic acid ester can be selectively hydrolyzed, allowing (1S,2R)-2-chloro-2-fluorocyclopropanecarboxylic acid to be obtained with a high yield and excellent selectivity.

The enzyme of the present invention may be used in various forms, such as a purified enzyme, a crude enzyme, a microbial culture, a microbial cell, and a processed product thereof. Here, a processed product means, for example, lyophilized microbial cells, acetone-dried microbial cells, ground microbial cells, autolyzed microbial cells, sonicated microbial cells, microbial cell extracts, and alkali treated microbial cells. It is also possible to use the aforementioned enzymes having various purities and forms after immobilizing them by a known method such as adsorption to silica gel, ceramics or a like inorganic carrier, cellulose, or ion exchange resin; a polyacrylamide method, a sulfur-containing polysaccharide gel method (for example, a carrageenan gel method), an alginic acid gel method, and an agar gel method.

The amount of the enzyme of the present invention may be suitably selected so as to prevent a prolonged reaction and reduction of the selectivity. For example, when a purified enzyme or a crude enzyme is used, the amount thereof is generally 0.001 to 2 times by weight, preferably 0.002 to 0.5 times by weight, more preferably 0.005 to 0.2 times by weight, and even more preferably 0.005 to 0.1 times by weight relative to that of (1S)-2-chloro-2-fluorocyclopropanecarboxylic acid ester. When a microbial culture, microbial cell, or processed product thereof is used, the amount thereof is generally 0.01 to 200 times by weight, and preferably 0.1 to 50 times by weight relative to that of (1S)-2-chloro-2-fluorocyclopropanecarboxylic acid ester. Use of the enzyme of the present invention in an amount within the aforementioned range allows (1S,2R)-2-chloro-2-fluorocyclopropanecarboxylic acid to be obtained with excellent selectivity and without a prolonged reaction.

The reaction is carried out in the presence of water. Water is used in the form of a sodium phosphate aqueous solution, a potassium phosphate aqueous solution, a sodium hydrogen carbonate aqueous solution, or a like buffer solution of inorganic salts; or a sodium acetate aqueous solution, a sodium citrate aqueous solution, or a like buffer solution of organic salts. Use as a buffer solution of inorganic salts is preferred and a sodium phosphate aqueous solution or a sodium hydrogen carbonate aqueous solution is particularly preferred. The concentration of the buffer solution is not limited and is generally 5 mol/L or less, and preferably within the range of 0.01 to 2 mol/L. The amount of water is not limited, and is generally 1 to 100 times by weight, preferably 1 to 50 times by weight, and more preferably 3 to 30 times by weight relative to the amount of (1S)-2-chloro-2-fluorocyclopropanecarboxylic acid ester.

The enzymatic hydrolysis of the present invention may be carried out in the presence of a hydrophobic organic solvent, a hydrophilic organic solvent, or a like organic solvent. Examples of hydrophobic organic solvents include tert-butyl methyl ether, isopropyl ether and like ethereal solvents; and toluene, hexane, cyclohexane, heptane and like hydrocarbon solvents. Examples of hydrophilic organic solvents include tert-butanol, methanol, ethanol, isopropanol, isobutanol, n-butanol, and like alcohol solvents; tetrahydrofuran and like ethereal solvents; dimethylsulfoxide and like sulfoxide solvents; acetone and like ketone solvents; acetonitrile and like nitrile solvents; and N,N-dimethyl formamide and like amide solvents. These hydrophobic organic solvents and hydrophilic organic solvents may be used singly or in a combination of two or more.

When an organic solvent is used, the amount thereof is generally 100 times by weight or less, and preferably within the range of 0.1 to 50 times by weight relative to that of (1S)-2-chloro-2-fluorocyclopropanecarboxylic acid ester.

The enzymatic hydrolysis of the present invention is generally conducted by mixing water or a buffer solution, (1S)-2-chloro-2-fluorocyclopropanecarboxylic acid ester and the enzyme of the present invention. They may be added in any order.

The reaction temperature is generally 0 to 100° C., preferably 10 to 60° C., and more preferably 30 to 50° C. The reaction time varies depending on the reaction temperature, and falls within the range of generally 1 hour to 7 days, and preferably 2 hours to 72 hours. The proceeding of the reaction can be confirmed by thin layer chromatography, gas chromatography, high-performance liquid chromatography, or a like commonly used analytic technique.

The pH of the mixture during the reaction is generally 4 to 10, preferably 5 to 9, and more preferably 6 to 8. During the reaction, the pH may be adjusted to a desirable range by adding a base. Examples of usable bases include sodium hydroxide, potassium hydroxide, and like alkali metal hydroxides; sodium carbonate, potassium carbonate, and like alkali metal carbonates; calcium carbonate and like alkaline earth metal carbonates; sodium hydrogen carbonate, potassium hydrogen carbonate, and like alkali metal hydrogen carbonates; sodium dihydrogen phosphate, disodium hydrogen phosphate, potassium dihydrogen phosphate, dipotassium hydrogen phosphate, and like alkali metal phosphates; triethylamine, pyridine, and like organic bases; and ammonia. These bases may be used singly or in a combination of two or more. These bases are generally used in the form of an aqueous solution, but may be in a solid form or may be suspended in a solution.

The reaction mixture after the completion of the reaction contains (1S,2R)-2-chloro-2-fluorocyclopropanecarboxylic acid, and post-processing is generally conducted to separate it from the enzyme used in the reaction, the buffer, the unreacted (1S)-2-chloro-2-fluorocyclopropanecarboxylic acid ester, etc.

Post-processing may be carried out by, for example, a method wherein the reaction mixture is concentrated if necessary and then separation/purification is conducted using silica gel chromatography, a method wherein separation/purification is conducted by distillation after concentration, or a method wherein separation/purification is conducted by liquid-liquid separation after concentration.

In the case where separation/purification is conducted by liquid-liquid separation, if an organic solvent that is soluble both in water and a hydrophobic organic solvent is used during the reaction, liquid-liquid separation may be conducted after removing the organic solvent by distillation. If the reaction mixture contains an insoluble enzyme, immobilization support and the like, liquid-liquid separation may be conducted after removing these substances by filtration.

In order to isolate the objective (1S,2R)-2-chloro-2-fluorocyclopropanecarboxylic acid from the unreacted (1S)-2-chloro-2-fluorocyclopropanecarboxylic acid ester by liquid-liquid separation, the (1S,2R)-2-chloro-2-fluorocyclopropanecarboxylic acid should be extracted into a water layer in the form of a salt by using a hydrophobic organic solvent and water and adjusting the pH of the water layer to basic, and then the water layer is separated from the organic layer.

Examples of hydrophobic organic solvents include tert-butyl methyl ether, isopropyl ether, and like ethereal solvents; toluene and like aromatic hydrocarbon solvents; hexane, cyclohexane, heptane, and like aliphatic hydrocarbon solvents;

dichloromethane, dichloroethane, chloroform, chlorobenzene, ortho-dichlorobenzene, and like halogenated hydrocarbon solvents; ethyl acetate, methyl acetate, butyl acetate, and like ester solvents; and methyl isobutyl ketone and like ketone solvents. When a hydrophobic organic solvent was used during the reaction, liquid-liquid separation may be conducted without any additional treatment.

The pH of the water layer used for extraction for the purpose described above is generally 8 or more, and preferably within the range of 10 to 14. In order to adjust the pH value, a base may be used. Usable bases are the same as those usable for adjusting the pH during the reaction.

In order to isolate the (1S,2R)-2-chloro-2-fluorocyclopropanecarboxylic acid from the enzyme, the buffer, and like water-soluble components used in the reaction by liquid-liquid separation, the (1S,2R)-2-chloro-2-fluorocyclopropanecarboxylic acid should be extracted into the organic layer by using a hydrophobic organic solvent and water and adjusting the pH of the water layer to acidic, and then the organic layer is separated from the water layer.

The pH of the water layer used for extraction for the purpose described above is generally 7 or less, and preferably within the range of 0.1 to 3. In order to adjust the pH, an acid may be used. Examples of usable acids include hydrogen chloride, hydrogen bromide, sulfuric acid, phosphoric acid, and like inorganic acids; acetic acid, citric acid, methanesulfonic acid, and like organic acids; and salts thereof.

The objective (1S,2R)-2-chloro-2-fluorocyclopropanecarboxylic acid can be isolated by subjecting an aqueous solution or an organic solvent solution containing the resulting (1S,2R)-2-chloro-2-fluorocyclopropanecarboxylic acid to concentration or crystallization. The isolated (1S,2R)-2-chloro-2-fluorocyclopropanecarboxylic acid may be further purified by re-crystallization, distillation, column chromatography, or a like ordinary purification treatment.

Examples of solvents used for crystallizing or re-crystallizing (1S,2R)-2-chloro-2-fluorocyclopropanecarboxylic acid include n-hexane, n-pentane, and like aliphatic hydrocarbon solvents; benzene, toluene, xylene, and like aromatic hydrocarbon solvents; methanol, ethanol, propanol, isopropanol, n-butanol, and like alcohol solvents; diethyl ether, tetrahydrofuran, dimethoxyethane, and like ethereal solvents; chloroform, dichloromethane, dichloroethane, and like halogenated hydrocarbon solvents; dimethylformamide, dimethylacetamide, and like amide solvents; acetonitrile and like nitrile solvents; ethyl acetate and like ester solvents; and water. These solvents may be used singly or in a combination of two or more. The amount of the solvent is generally 2 to 100 times the total amount of the solid components in the (1S,2R)-2-chloro-2-fluorocyclopropanecarboxylic acid used.

When (1S,2R)-2-chloro-2-fluorocyclopropanecarboxylic acid is supplied to the reduction described later, the reaction mixture before post-processing may be supplied to the reduction; however, the reaction mixture is generally supplied to the reduction after being subjected to post-processing. After conducting post-processing, (1S,2R)-2-chloro-2-fluorocyclopropanecarboxylic acid may be supplied to the reduction in the form of an aqueous solution or an organic solvent solution containing (1S,2R)-2-chloro-2-fluorocyclopropanecarboxylic acid or it may be supplied to the reduction in the form of an isolated or purified (1S,2R)-2-chloro-2-fluorocyclopropanecarboxylic acid.

2. Method for producing (1S,2S)-2-fluorocyclopropanecarboxylic acid

The method for producing (1S,2S)-2-fluorocyclopropanecarboxylic acid by reducing (1S,2R)-2-chloro-2-fluorocyclopropanecarboxylic acid is explained below.

The reduction may be carried out by using, for example, zinc, a trialkyltin hydride compound, a metal boron hydride compound and a Lewis acid in the presence of an aprotic polar solvent and a nickel-aluminum alloy. The reduction may also be performed through hydrogenation using palladium/carbon, and hydrogenation using sponge nickel, etc. Among various methods, reduction using a nickel-aluminum alloy and hydrogenation using sponge nickel are preferred, and reduction using a nickel-aluminum alloy is particularly preferred.

Reduction using a nickel-aluminum alloy (hereunder referred to as development reduction and hydrogenation using sponge nickel (hereunder referred to as hydrogenation) are explained below.

2.1 Development Reduction

Development reduction is conducted by allowing a base to react with a nickel-aluminum alloy in the presence of (1S,2R)-2-chloro-2-fluorocyclopropanecarboxylic acid.

The development reduction is generally conducted in the presence of a solvent. Water is typically used as the solvent. Organic solvents, such as methanol, ethanol, propanol, isopropanol, n-butyl alcohol, tert-butanol, and like alcohol solvents; acetone and like ketone solvents; and tert-butyl methyl ether and like ethereal solvents may be used together with water. It is preferred to use water singly. Although not particularly limited, the amount of the solvent is generally within the range of not more than 100 times by weight, preferably 1 to 50 times by weight, and more preferably 1 to 5 times by weight, relative to (1S,2R)-2-chloro-2-fluorocyclopropanecarboxylic acid.

A commercially available nickel-aluminum alloy may be used. The content of nickel in the alloy is generally 30 to 60 weight %, and preferably 40 to 50 weight %. The amount of the nickel used is within the range of generally not more than 5 times by weight, preferably 0.1 to 1 time by weight, and more preferably 0.2 to 0.5 times by weight relative to (1S,2R)-2-chloro-2-fluorocyclopropanecarboxylic acid.

Although an organic base may be used as the base, an inorganic base is generally used.

Examples of inorganic bases include sodium hydroxide, potassium hydroxide, and like alkali metal hydroxides. The inorganic base is generally used in the form of an aqueous solution. The concentration of such an aqueous solution may be suitably selected, and is generally 10 to 50 weight %, preferably 15 to 35 weight %, and more preferably 20 to 30 weight %. The amount of inorganic base is generally 15 times by mol or less, preferably 0.1 to 5 times by mol, and more preferably 1 to 3 times by mol relative to the amount of (1S,2R)-2-chloro-2-fluorocyclopropanecarboxylic acid.

At least one base selected from the group consisting of ammonia, hydrazine and organic bases may be used together with the inorganic base. Examples of organic bases include methylamine, ethylamine, dimethylamine, diethylamine, and like alkyl amines; ethanolamine, isopropanolamine, and like amino alcohols; and ethylenediamine and like alkylenediamines. Among the bases selected from the group consisting of ammonia, hydrazine and organic bases, ammonia, methylamine, ethanolamine, and ethylenediamine are preferable, and ammonia and ethylenediamine are particularly preferable.

The amount of the at least one base selected from the group consisting of ammonia, hydrazine and organic bases is generally 15 times by mol or less, preferably 0.5 to 5 times by mol, and more preferably 1 to 2 times by mol relative to the amount of (1S,2R)-2-chloro-2-fluorocyclopropanecarboxylic acid.

The reaction temperature of the development reduction is generally 0 to 100° C., preferably 20 to 80° C., and more preferably 30 to 60° C. The reaction time varies depending on the reaction temperature, but generally falls within the range of 1 minute to 48 hours. The proceeding of the reaction can be monitored by thin layer chromatography, gas chromatography, high-performance liquid chromatography, or a like commonly used analytic technique.

There is no particular limitation to the order of adding (1S,2R)-2-chloro-2-fluorocyclopropanecarboxylic acid, a nickel-aluminum alloy and a base. A preferable embodiment is to mix (1S,2R)-2-chloro-2-fluorocyclopropanecarboxylic acid and a nickel-aluminum alloy first, and to then add a base to the resulting mixture. In this reaction, it is preferable that the base be added gradually. The reaction may be conducted under atmospheric pressure or pressurized conditions.

2.2 Hydrogenation

Hydrogenation is generally conducted by mixing (1S,2R)-2-chloro-2-fluorocyclopropanecarboxylic acid and sponge nickel in the presence of a solvent, and stirring the resulting mixture under a hydrogen atmosphere. In the hydrogenation, a base may be added if necessary.

Water is generally used as the solvent. An organic solvent may also be used together with water. Examples of usable organic solvents include methanol, ethanol, propanol, isopropanol, n-butyl alcohol, tert-butanol, and like alcohol solvents; diethyl ether, diisopropyl ether, 1,4-dioxane, tetrahydrofuran, tert-butyl methyl ether, and like ethereal solvents; toluene and like aromatic hydrocarbon solvents; and hexane, cyclohexane, and like aliphatic hydrocarbon solvents. The use of water singly is preferred. The amount of the solvent is not particularly limited, and is generally 100 times by weight or less, preferably 1 to 50 times by weight, and more preferably 1 to 5 times by weight relative to the amount of (1S,2R)-2-chloro-2-fluorocyclopropanecarboxylic acid. The amount of the solvent is not particularly limited, and is generally 100 times by weight or less, preferably 1 to 50 times by weight, and more preferably 1 to 10 times by weight relative to the amount of (1S,2R)-2-chloro-2-fluorocyclopropanecarboxylic acid.

A commercially available sponge nickel is generally used, but the sponge nickel may be prepared by any known method. The amount of sponge nickel is generally 10 times by weight or less, preferably 0.1 to 5 times by weight, and more preferably 0.2 to 2 times by weight calculated as pure nickel relative to the amount of (1S,2R)-2-chloro-2-fluorocyclopropanecarboxylic acid.

Generally, at least one member selected from the group consisting of alkali metal hydrides and alkali metal carbonates is used as the base. At the same time, at least one member selected from the group consisting of ammonia and organic bases may be used in combination with the base.

Examples of alkali metal hydroxides include sodium hydroxide, potassium hydroxide, and lithium hydroxide. Examples of alkali metal carbonates include potassium carbonate, etc. These bases are generally used in the form of an aqueous solution. The concentration of the aqueous solution may be suitably selected, and is generally 10 to 50 weight %, preferably 15 to 35 weight %, and more preferably 20 to 30 weight %.

Examples of organic bases include methylamine, ethylamine, dimethylamine, diethylamine, and like alkylamines; ethanolamine, isopropanolamine, and like amino alcohols; ethylenediamine and like alkylenediamines; and pyridine, piperidino, and like saturated or aromatic heterocyclic amines. Among these, methylamine, ethanolamine and ethylenediamine are preferable, and ethylenediamine is particularly preferable.

The amount of the base is generally 20 times by mol or less, preferably 0.1 to 5 times by mol, and more preferably 0.5 to 2 times by mol relative to the amount of (1S,2R)-2-chloro-2-fluorocyclopropanecarboxylic acid.

The reaction temperature of the hydrogenation is generally 0 to 100° C., preferably 20 to 80° C., and more preferably 30 to 60° C. The reaction time varies depending on the reaction temperature, and is generally within the range of 1 minute to 48 hours. The proceeding of the reaction can be monitored by thin layer chromatography, gas chromatography, high-performance liquid chromatography, or a like generally used analytic technique.

A commercial available hydrogen gas is generally used as the hydrogen. The pressure of the hydrogen is generally 0.1 to 10 MPa, and preferably 0.1 to 1 MPa.

The reaction mixture after the completion of the reduction contains (1S,2S)-2-fluorocyclopropanecarboxylic acid. In order to remove the catalyst, the base, and the like used during the reduction, the reaction mixture is subjected to post-processing.

Examples of post-processing include filtration treatment and like solid-liquid separation treatments, and a liquid-liquid separation treatment. The liquid-liquid separation treatment can be carried out in the same manner as in the post-processing for the aforementioned enzymatic hydrolysis of the present invention.

(1S,2S)-2-Fluorocyclopropanecarboxylic acid can be isolated by subjecting the reaction mixture to post-processing and subjecting the mixture thus obtained to concentration, crystallization, or a like ordinary isolation treatment. The isolated (1S,2S)-2-fluorocyclopropanecarboxylic acid may be further purified by an ordinary purification treatment such as re-crystallization, distillation, and column chromatography. In this reaction, the crystallization or re-crystallization may be performed in the same manner as for the crystallization or re-crystallization of (1S,2R)-2-chloro-2-fluorocyclopropanecarboxylic acid described above.

EXAMPLES

The present invention is described in detail below with reference to Examples. However, the scope of the present invention is not limited by these Examples.

In the following Production Examples and Examples, the yield, anti/syn ratio, cis/trans ratio, optical purity and chemical purity of each resulting product were obtained in the manner described below.
Ethyl diazoacetate
Yield: Gas chromatography analysis
Column: DB-WAX
0.53 mm×30 m, membrane thickness of 1.0 μm (Produced by Agilent Technologies, Inc.)

(1S)-2-Chloro-2-fluorocyclopropanecarboxylic acid ethyl ester

Yield and anti/syn ratio: Gas chromatography analysis
Column: DB-WAX
0.25 mm×30 m, membrane thickness of 0.25 μm (Produced by Agilent Technologies, Inc.)
Optical purity: Gas chromatography analysis
Column: InertCap (registered trademark) CHIRAMIX
0.25 mm×30 m, membrane thickness of 0.25 μm (Produced by GL Sciences, Inc.); or
CP-Cyclodextrin-β-2,3,6-M-19
0.25 mm×50 m, membrane thickness of 0.25 μm (Produced by GL Sciences, Inc.)

(1S,2R)-2-Chloro-2-fluorocyclopropanecarboxylic acid

Yield and anti/syn ratio: High-performance liquid chromatography analysis
Column: L-column 2 (registered trademark)
4.6 mm×250 mm, 5 μm (Produced by Chemicals Evaluation and Research Institute)
Eluent: An aqueous solution obtained by adding phosphoric acid to a $KH_2PO_4$ aqueous solution (5 mmol/L) and adjusting its pH value to 2.5, and acetonitrile
Optical purity: Gas chromatography analysis
Column: InertCap (registered trademark) CHIRAMIX
0.25 mm×30 m, membrane thickness of 0.25 μm (Produced by GL Sciences, Inc.)
Method: Analysis was conducted after derivatizing (1S,2R)-2-chloro-2-fluorocyclopropanecarboxylic acid to methyl ester using trimethylsilyldiazomethane.

(1S,2S)-2-Fluorocyclopropanecarboxylic acid

Yield and cis/trans ratio: High-performance liquid chromatography analysis
Column: L-column 2 (registered trademark)
4.6 mm×250 mm, 5 μm (Produced by Chemicals Evaluation and Research Institute)
Eluent: An aqueous solution obtained by adding phosphoric acid to a $KH_2PO_4$ aqueous solution (5 mmol/L) and adjusting its pH value to 2.5, and acetonitrile
Optical purity: Gas chromatography analysis
Column: InertCap (registered trademark) CHIRAMIX
0.25 mm×30 m, membrane thickness of 0.25 μm (Produced by GL Sciences, Inc.)
Method: Analysis was conducted after derivatizing (1S,2S)-2-fluorocyclopropanecarboxylic acid to methyl ester using trimethylsilyldiazomethane.
Chemical purity and cis/trans ratio: Gas chromatography analysis
Column: HR-20M
0.53 mm×30 m, membrane thickness of 1.0 μm (Produced by Shinwa Chemical Industries, Ltd.)

In each example below, (1S)-2-chloro-2-fluorocyclopropanecarboxylic acid or an ester thereof having an anti configuration means that the chlorine atom is located on the opposite side of the cyclopropane plane to the carboxyl or alkoxycarbonyl group, and a syn configuration means that the chlorine atom and the carboxyl or alkoxycarbonyl group are located on the same side of the cyclopropane plane. For example, (1S,2R)-2-chloro-2-fluorocyclopropanecarboxylic acid has an anti configuration. When (1S)-2-fluorocyclopropanecarboxylic acid is a cis isomer, the fluorine atom and the carboxyl group are located on the same side of the cyclopropane plane, and when it is a trans isomer, the fluorine atom and the carboxyl group are located on opposite sides of the cyclopropane plane. For example, (1S,2S)-2-fluorocyclopropanecarboxylic acid is a cis isomer.

Production Example 1

Ethyl Diazoacetate

Under a nitrogen atmosphere, 318 g of water, 188 g (1.35 mol) of glycine ethyl ester hydrochloride, and 188 g of n-heptane were sequentially supplied, and the resulting mixture was then cooled to 10° C. To the mixture, 1.74 g of 28 weight % sodium hydroxide aqueous solution was added to adjust its pH to 4.7. While keeping the internal temperature at 10±2° C., 279 g of 40 weight % sodium nitrite aqueous solution (net: 112 g, 1.62 mol) and a citric acid aqueous solution containing 4.54 g (0.0216 mol) of citric acid monohydrate and 65.8 g of water were simultaneously added dropwise over a period of 3 hours to the mixture obtained above. The resulting mixture was kept at 10° C. for 6 hours, and a sodium carbonate aqueous solution containing 6.58 g (0.0621 mol) of sodium carbonate and 87.5 g of water was added to the mixture dropwise. The mixture thus obtained was subjected to liquid-liquid separation wile maintaining the internal temperature at 10±5° C. The organic layer obtained was dried using 6.2 g of a 4 A molecular sieve and then subjected to filtration, obtaining 341 g of a n-heptane solution of ethyl diazoacetate (content: 38.0 weight %, net: 129 g, yield: 84.1%).

Production Example 2

Ethyl Diazoacetate

Under a nitrogen atmosphere, 212 g of water, 126 g (0.900 mol) of glycine ethyl ester hydrochloride, and 126 g of n-hexane were sequentially supplied, and the resulting mixture was then cooled to 10° C. To the mixture, 1.99 g of 28 weight % sodium hydroxide aqueous solution was added to adjust its pH to 4.9. While keeping the internal temperature at 10±2° C., 186 g of 40 weight % sodium nitrite aqueous solution (net: 74.5 g, 1.08 mol) and a citric acid aqueous solution containing 3.03 g (0.0144 mol) of citric acid monohydrate and 43.9 g of water were simultaneously added dropwise for a period of over 2 hours to the mixture obtained above. The resulting mixture was kept at 10° C. for 7 hours, and a sodium carbonate aqueous solution containing 4.39 g (0.0414 mol) of sodium carbonate and 58.3 g of water was added to the mixture dropwise. The mixture thus obtained was subjected to liquid-liquid separation wile maintaining the internal temperature at 10±5° C., obtaining 213 g of n-hexane solution of ethyl diazoacetate (content: 41.0 weight %, net: 87.2 g, yield: 84.9%).

Production Example 3

Distillation of Ethyl Diazoacetate

A n-hexane solution of ethyl diazoacetate obtained in Production Example 2 (213 g, content: 41.0 weight %, net: 87.2 g) was concentrated at a temperature of 38° C. to 42° C. and a reduced pressure of 200 hPa to 370 hPa. The resulting residue was subjected to distillation at a temperature of 52° C. to 60° C. and a reduced pressure of 12.0 hPa to 31 hPa, obtaining 70.1 g of ethyl diazoacetate (content: 96.5 weight %, net: 67.7 g) in the form of a yellow oily substance.

Production Example 4

Ethyl Diazoacetate

Under a nitrogen atmosphere, 637 g of water, 377 g (2.70 mol) of glycine ethyl ester hydrochloride, and 377 g of n-heptane were sequentially supplied, and the resulting mixture was then cooled to 10° C. To the mixture, 3.14 g of 26 weight % sodium hydroxide aqueous solution was added to adjust its pH to 4.7. While keeping the internal temperature at 10±2° C., 559 g of 40 weight % sodium nitrite aqueous solution (net: 224 g, 3.24 mol) and a citric acid aqueous solution containing 17.0 g (0.0810 mol) of citric acid monohydrate and 247 g of water were simultaneously added dropwise over a period of 15 hours to the mixture obtained above. The resulting mixture was kept at 10° C. for 4 hours, and a sodium carbonate aqueous solution containing 24.0 g (0.227 mol) of sodium carbonate and 277 g of water was added to the mixture dropwise. The mixture thus obtained was subjected to liquid-liquid separation while maintaining the internal temperature at 10±5° C. The organic layer obtained was dried using 12.4 g of a 4 A molecular sieve and then subjected to filtration, obtaining 672 g of a n-heptane solution of ethyl diazoacetate (content: 38.0 weight %, net: 255 g, yield: 82.9%).

Example 1

(1S)-2-Chloro-2-fluorocyclopropanecarboxylic acid ethyl ester 2,2-Bis[2-[(4S)-tert-butyloxazoline]]propane (1.79 g, 6.06 mmol), copper (II) trifluoromethanesulfonate (1.98 g, 5.50 mmol) and n-heptane (35.5 g) were placed in a 1,300-mL autoclave under a nitrogen atmosphere at an ordinary temperature. While stirring the resulting mixture, the reaction vessel was cooled to 0° C. After sealing the vessel, 1-chloro-1-fluoroethylene (177 g, 2.19 mol) was supplied thereto under pressure, followed by adjusting the internal temperature to 5±2° C. While keeping the internal temperature at 5±2° C., 327 g of a n-heptane solution of the ethyl diazoacetate obtained in Production Example 1 (content: 38.0 weight %, net: 124 g, 1.09 mol) was added dropwise thereto over a period of 5 hours, and the resulting mixture was stirred at the same temperature for 1 hour. When the internal pressure exceeded 1 MPa during the dropwise addition with the temperature retained, a purge operation was conducted to keep the pressure within the range of 0.9 MPa to 1 MPa. After resetting the pressure to ordinary pressure, the temperature was increased and the atmosphere was then replaced with a nitrogen atmosphere. The reaction mixture thus prepared was washed with 27 g of a 0.5 mol/L ethylenediaminetetraacetic acid aqueous solution to conduct liquid-liquid separation, obtaining 453 g of a mixture containing (1S)-2-chloro-2-fluorocyclopropanecarboxylic acid ethyl ester (content: 27.5 weight %, net: 125 g, yield: 68.6% (relative to ethyl diazoacetate), anti/syn ratio=62.5/37.5, optical purity of anti configuration=98.2% ee, optical purity of syn configuration=97.4% ee). The components that adhered to the autoclave and like instruments used in the reaction were dissolved in acetonitrile to conduct content analysis. The analysis revealed that the total amount of (1S)-2-chloro-2-fluorocyclopropanecarboxylic acid ethyl ester was 1.3% converted into the yield. Accordingly, the reaction yield was 69.9%.

Example 2

(1S)-2-Chloro-2-fluorocyclopropanecarboxylic acid ethyl ester 2,2-Bis[2-[(4S)-tert-butyloxazoline]]propane (811 mg, 2.75 mmol), copper (II) trifluoromethanesulfonate (903 mg, 2.50 mmol) and n-heptane (16.3 g) were placed in a 1,300-mL autoclave under a nitrogen atmosphere at an ordinary temperature. While stirring the resulting mixture, the reaction vessel was cooled to 0° C. After sealing the vessel, 1-chloro-1-fluoroethylene (203 g, 2.52 mol) was supplied thereto under pressure, followed by adjusting the internal temperature to 5±2° C. While keeping the internal temperature at 5±2° C., 149 g of a n-heptane solution of the ethyl diazoacetate obtained according to Production Example 1 (content: 38.3 weight %, net: 57.0 g, 0.500 mol) was added dropwise thereto over a period of 5 hours, and the resulting mixture was stirred at the same temperature for 1 hour. The internal pressure increased in accordance with the progress of the dropwise addition and finally reached 1.3 MPa. After resetting the pressure, the temperature was increased and the atmosphere was then replaced with a nitrogen atmosphere. The reaction mixture thus prepared was washed with 13 g of a 0.5 mol/L ethylenediaminetetraacetic acid aqueous solution to conduct liquid-liquid separation, obtaining 206 g of a mixture containing (1S)-2-chloro-2-fluorocyclopropanecarboxylic acid ethyl ester (content: 32.5 weight %, net: 66.9 g, yield: 80.2% (relative to ethyl diazoacetate), anti/syn ratio=62.4/37.6, optical purity of anti configuration=98.3% ee, optical purity of syn configuration=97.5% ee). The components that adhered to the autoclave and like instruments used in the reaction were dissolved in acetonitrile to conduct content analysis. The analysis revealed that the total amount of (1S)-2-chloro-2-fluorocyclopropanecarboxylic acid ethyl ester was 1.5% converted into the yield. Accordingly, the reaction yield was 81.7%.

Example 3

(1S)-2-Chloro-2-fluorocyclopropanecarboxylic acid ethyl ester 2,2-Bis[2-[(4S)-Cert-butyloxazoline]]propane (1.03 g, 3.48 mmol), copper (II) trifluoromethanesulfonate (1.14 g, 3.16 mmol) and n-heptane (20.5 g) were placed in a 1300 mL-autoclave under a nitrogen atmosphere at an ordinary temperature. While stirring the resulting mixture, the reaction vessel was cooled to 0° C. After sealing the vessel, 1-chloro-1-fluoroethylene (154 g, 1.91 mol) was supplied thereto under pressure, followed by adjusting the internal temperature to 5±2° C. While keeping the internal temperature at 5±2° C., 189 g of a n-heptane solution of the ethyl diazoacetate obtained according to Production Example 1 (content: 38.1 weight %, net: 71.9 g, 0.630 mol) was added dropwise thereto over a period of 5 hours, and the resulting mixture was stirred at the same temperature for 1 hour. The internal pressure increased in accordance with the progress of the dropwise addition and finally reached 1.5 MPa. After resetting the pressure, the temperature was increased and the atmosphere was then replaced with a nitrogen atmosphere. The reaction mixture thus prepared was washed with 15.8 g of a 0.5 mol/L ethylenediaminetetraacetic acid aqueous solution to conduct liquid-liquid separation, obtaining 269 g of a mixture containing (1S)-2-chloro-2-fluorocyclopropanecarboxylic acid ethyl ester (content: 27.1 weight %, net: 73.0 g, yield: 69.5% (relative to ethyl diazoacetate), anti/syn ratio=62.6/37.4, optical purity of anti configuration=98.2% ee, optical purity of syn configuration=97.5% ee). The components that adhered to the autoclave and like instruments used in the reaction were dissolved in acetonitrile to conduct content analysis. The analysis revealed that the total amount of (1S)-2-chloro-2- fluorocyclopropanecarboxylic acid ethyl ester was 0.9% converted into the yield. Accordingly, the reaction yield was 70.4%.

Example 4

(1S)-2-Chloro-2-fluorocyclopropanecarboxylic acid ethyl ester 2,2-Bis[2-[(4S)-Cert-butyloxazoline]]propane (0.809 g, 2.75 mmol), copper (II) trifluoromethanesulfonate (0.903 g, 2.50 mmol) and n-heptane (16.3 g) were placed in a 1,300-mL autoclave under a nitrogen atmosphere at an ordinary temperature. While stirring the resulting mixture, the reaction vessel was cooled to 0° C. After sealing the vessel, 1-chloro-1-fluoroethylene (202 g, 2.51 mol) was supplied thereto under pressure, followed by adjusting the internal temperature to 5±2° C. While keeping the internal temperature at 5±2° C., 146 g of a n-heptane solution of the ethyl diazoacetate obtained according to Production Example 1 (content: 39.2 weight %, net: 57.0 g, 0.500 mol) was added dropwise thereto over a period of 5 hours, and the resulting mixture was stirred at the same temperature for 1 hour. The internal pressure increased in accordance with the progress of the dropwise addition and finally reached 1.2 MPa. After resetting the pressure, the temperature was increased and the atmosphere was then replaced with a nitrogen atmosphere. The reaction mixture thus prepared was washed with 12.5 g of a 0.5 mol/L ethylenediaminetetraacetic acid aqueous solution to conduct liquid-liquid separation, obtaining 201 g of a mixture containing (1S)-2-chloro-2-fluorocyclopropanecarboxylic acid ethyl ester (content: 30.8 weight %, net: 62.0 g, yield: 74.4% (relative to ethyl diazoacetate), anti/syn ratio=62.2/37.8, optical purity of anti configuration=98.2% ee, optical purity of syn configuration=97.5% ee). The components that adhered to the autoclave and like instruments used in the reaction were dissolved in acetonitrile to conduct content analysis. The analysis revealed that the total amount of (1S)-2-chloro-2-fluorocyclopropanecarboxylic acid ethyl ester was 6.5% converted into the yield. Accordingly, the reaction yield was 80.9%.

Example 5

(1S)-2-Chloro-2-fluorocyclopropanecarboxylic acid ethyl ester 2,2-Bis[2-[(4S)-tert-butyloxazoline]]propane (0.520 g, 1.77 mmol), copper (II) trifluoromethanesulfonate (0.579 g, 1.61 mmol) and trifluorotoluene (42.0 g) were placed in a 260 mL-autoclave under a nitrogen atmosphere at an ordinary temperature. While stirring the resulting mixture, the reaction vessel was cooled to 0° C. After sealing the vessel, 1-chloro-1-fluoroethylene (13.0 g, 0.162 mol) was supplied thereto under pressure, followed by adjusting the internal temperature to 5±2° C. While keeping the internal temperature at 5±2° C., a solution containing 9.49 g of the ethyl diazoacetate obtained in Production Example 3 (content: 96.5 weight%, net: 9.16 g, 0.0802 mol) and trifluorotoluene (42.0 g) was added dropwise thereto over a period of 5 hours, and the resulting mixture was stirred at the same temperature for 1 hour. The internal pressure increased in accordance with the progress of the dropwise addition and finally reached 1.0 MPa. After resetting the pressure, the temperature was increased and the atmosphere was then replaced with a nitrogen atmosphere. The reaction mixture thus prepared was washed with 8.0 g of a 0.5 mol/L ethylenediaminetetraacetic acid aqueous solution to conduct liquid-liquid separation, obtaining 107 g of a mixture containing (1S)-2-chloro-2-fluorocyclopropanecarboxylic acid ethyl ester (content: 3.96 weight %, net: 4.22 g, yield: 31.6% (relative to ethyl diazoacetate), anti/syn ratio=62.0/40.0, optical purity of anti configuration=97.9% ee, optical purity of syn configuration=97.1% ee).

Example 6

(1S)-2-Chloro-2-fluorocyclopropanecarboxylic acid ethyl ester 2,2-Bis[2-[(4S)-tert-butyloxazoline]]propane (0.025 g, 0.085 mmol), copper (II) trifluoromethanesulfonate (0.027 g, 0.075 mmol) and trifluorotoluene (7.9 g) were placed in a 50 mL-autoclave under a nitrogen atmosphere at an ordinary temperature. While stirring the resulting mixture, the reaction vessel was cooled to 0° C. After sealing the vessel, 1-chloro-1-fluoroethylene (2.43 g, 0.0302 mol) was supplied thereto under pressure, followed by adjusting the internal temperature to 5±2° C. While keeping the internal temperature at 5±2° C., a solution containing 1.77 g of the ethyl diazoacetate obtained in Production Example 3 (content: 96.5 weight %, net: 1.71 g, 0.0150 mol) and trifluorotoluene (7.9 g) was added dropwise thereto over a period of 5 hours, and the resulting mixture was stirred at the same temperature for 1 hour. The internal pressure increased in accordance with the progress of the dropwise addition and finally reached 1.0 MPa. After resetting the pressure, the temperature was increased and the atmosphere was then replaced with a nitrogen atmosphere. The reaction mixture thus prepared was washed with 0.38 g of a 0.5 mol/L ethylenediaminetetraacetic acid aqueous solution to conduct liquid-liquid separation, obtaining 19.7 g of a mixture containing (1S)-2-chloro-2-fluorocyclopropanecarboxylic acid ethyl ester (content: 5.14 weight %, net: 1.01 g, yield: 40.5% (relative to ethyl diazoacetate), anti/syn ratio=60.4/39.6, optical purity of anti configuration=96.5% ee, optical purity of syn configuration=95.8% ee).

Example 7

(1S)-2-Chloro-2-fluorocyclopropanecarboxylic acid ethyl ester 2,2-Bis[2-[(4S)-tert-butyloxazoline]]propane (0.025 g, 0.085 mmol), copper (II) trifluoromethanesulfonate (0.027 g, 0.075 mmol) and trifluorotoluene (7.9 g) were placed in a 50 mL-autoclave under a nitrogen atmosphere at an ordinary temperature, and the resulting mixture was stirred. After sealing the reaction vessel, about 10% of a solution containing 1.77 g of the ethyl diazoacetate (content: 96.5 weight %, net: 1.71 g, 0.0150 mol) obtained in Production Example 3 and 7.9 g of trifluorotoluene was added to the mixture obtained above dropwise over a period of 30 minutes. The mixture was stirred for 5 minutes and the reaction vessel was then cooled to 0° C. Thereafter, 1-chloro-1-fluoroethylene (2.46 g, 0.0306 mol) was supplied to the reaction vessel under pressure, followed by adjusting the internal temperature to 5±2° C. While keeping the internal temperature at 5±2° C., the remaining 90% of the ethyl diazoacetate prepared above was added thereto dropwise over a period of 4.5 hours. The resulting mixture was stirred at the same temperature for 1 hour. The internal pressure increased in accordance with the progress of the dropwise addition and finally reached 0.9 MPa. After resetting the pressure, the temperature was increased and the atmosphere was then replaced with a nitrogen atmosphere. The reaction mixture thus prepared was washed with 0.38 g of a 0.5 mol/L ethylenediaminetetraacetic acid aqueous solution to conduct liquid-liquid separation, obtaining 19.7 g of a mixture containing (1S)-2-chloro-2-fluorocyclopropanecarboxylic acid ethyl ester (content: 4.47 weight %, net: 0.88 g, yield: 35.4% (relative to ethyl diazoacetate), anti/syn ratio=60.3/39.7, optical purity of anti configuration=94.6% ee, optical purity of syn configuration=93.6% ee).

Example 7-1

(1S)-2-chloro-2-fluorocyclopropanecarboxylic acid ethyl ester 2,2-Bis[2-[(4S)-tert-butyloxazoline]]propane (1.40 g, 4.75 mmol), copper (II) trifluoromethanesulfonate (1.56 g, 4.32 mmol) and n-heptane (35.7 g) were placed in a 1,300 mL-autoclave under a nitrogen atmosphere at an ordinary temperature. While stirring the resulting mixture, the reaction vessel was cooled to 0° C. After sealing the vessel, 1-chloro-1-fluoroethylene (173 g, 2.15 mol) was supplied thereto under pressure, followed by adjusting the internal temperature to 7±2° C. While keeping the internal temperature at 7±2° C., 315 g of a n-heptane solution of the ethyl diazoacetate obtained in Production Example 4 (content: 39.1 weight %, net: 123 g, 1.08 mol) was added dropwise thereto over a period of 24 hours, and the resulting mixture was stirred at the same temperature for 1 hour. When the internal pressure exceeded 1 MPa during the dropwise addition with the temperature retained, a purge operation was conducted to keep the pressure within the range of 0.9 MPa to 1 MPa. After resetting the pressure, the temperature was increased and the atmosphere was then replaced with a nitrogen atmosphere, obtaining 396 g of mixture containing (1S)-2-chloro-2-fluorocyclopropanecarboxylic acid ethyl ester (content: 26.7 weight %, net: 106 g, yield: 58.8% (relative to ethyl diazoacetate), anti/syn ratio=61.5/38.5, optical purity of anti configuration=97.8% ee, optical purity of syn configuration=96.9% ee). The components that adhered to the autoclave and like instruments used in the reaction were dissolved in tert-butyl methyl ether to conduct content analysis. The analysis revealed that the total amount of (1S)-2-chloro-2-fluorocyclopropanecarboxylic acid ethyl ester was 10.6% converted into the yield. Accordingly, the reaction yield was 69.4%.

Example 8

Distillation of (1S)-2-chloro-2-fluorocyclopropanecarboxylic acid ethyl ester Reactions were repeatedly conducted under conditions that were almost the same as those in Example 1. The mixture containing (1S)-2-chloro-2-fluorocyclopropanecarboxylic acid ethyl ester obtained in each reaction was united, to obtain 1,278 g of a mixture containing (1S)-2-chloro-2-fluorocyclopropanecarboxylic acid ethyl ester (content: 25.4 weight %, net: 325 g, anti/syn ratio=62.6/37.4, optical purity of anti configuration=98.2% ee). The solution thus obtained was concentrated at a temperature of 40° C. to 42° C. and a reduced pressure of 19 hPa to 106 hPa. The resulting residue was subjected to distillation at a temperature of 70° C. to 88° C. and a reduced pressure of 5.3 hPa to 14 hPa, to obtain 294 g of (1S)-2-chloro-2-fluorocyclopropanecarboxylic acid ethyl ester (content: 98.1 weight %, net: 289 g, anti/syn ratio=61.1/38.9, optical purity of anti configuration=98.2% ee) in the form of a colorless oily substance.

Example 9

Distillation of (1S)-2-chloro-2-fluorocyclopropanecarboxylic acid ethyl ester A mixture containing the (1S)-2-chloro-2-fluorocyclopropanecarboxylic acid ethyl ester obtained in Example 2 (206 g, content: 32.5 weight %, net: 66.9 g, anti/syn ratio=62.4/37.6, optical purity of anti configuration=98.3% ee) was concentrated at a temperature of 40° C. to 42° C. and a reduced pressure of 40 hPa to 133 hPa. The resulting residue was subjected to distillation at a temperature of 67° C. to 88° C. and a reduced pressure of 6.7 hPa to 13 hPa, to obtain 59.4 g of (1S)-2-chloro-2-fluorocyclopropanecarboxylic acid ethyl ester (content: 98.4 weight %, net: 58.4 g, anti/syn ratio=62.5/37.5, optical purity of anti configuration=98.3% ee) in the form of a colorless oily substance.

Example 10

Distillation of (1S)-2-chloro-2-fluorocyclopropanecarboxylic acid ethyl ester A mixture containing the (1S)-2-chloro-2-fluorocyclopropanecarboxylic acid ethyl ester obtained in Example 3 (269 g, content: 27.1 weight %, net: 72.8 g, anti/syn ratio =62.6/37.4, optical purity of anti configuration=98.2% ee) was concentrated at a temperature of 40° C. to 42° C. and a reduced pressure of 40 hPa to 133 hPa. The resulting residue was subjected to distillation at a temperature of 67° C. to 88° C. and a reduced pressure of 6.7 hPa to 13 hPa, to obtain 66.6 g of (1S)-2-chloro-2-fluorocyclopropanecarboxylic acid ethyl ester (content: 97.4 weight %, net: 64.9 g, anti/syn ratio=62.4/37.6, optical purity of anti configuration=98.2% ee) in the form of a colorless oily substance.

Example 11

Distillation of (1S)-2-chloro-2-fluorocyclopropanecarboxylic acid ethyl ester A mixture containing the (1S)-2-chloro-2-fluorocyclopropanecarboxylic acid ethyl ester obtained in Example 4 (201 g, content: 30.8 weight %, net: 62.0 g, anti/syn ratio=62.2/37.8, optical purity of anti configuration=98.2% ee) was concentrated at a temperature of 40° C. to 41° C. and a reduced pressure of 27 hPa to 101 hPa. The resulting residue was subjected to distillation at a temperature of 70° C. to 85° C. and a reduced pressure of 8.0 hPa to 27 hPa, to obtain 57.7 g of (1S)-2-chloro-2-fluorocyclopropanecarboxylic acid ethyl ester (content: 100 weight %, net: 57.7 g, anti/syn ratio=61.7/38.3, optical purity of anti configuration=98.2% ee) in the form of a colorless oily substance.

Example 12

Distillation of (1S)-2-chloro-2-fluorocyclopropanecarboxylic acid ethyl ester The mixtures containing (1S)-2-chloro-2-fluorocyclopropanecarboxylic acid ethyl ester obtained in Examples 5 to 7 were united, to obtain 121 g of a mixture containing (1S)-2-chloro-2-fluorocyclopropanecarboxylic acid ethyl ester (content: 4.1 weight %, net: 5.0 g, anti/syn ratio=60.4/39.6, optical purity of anti configuration=96.5% ee). The solution thus obtained was concentrated at a temperature of 35° C. to 40° C. and a reduced pressure of 20 hPa to 133 hPa. The resulting residue was subjected to distillation at a temperature of 82° C. to 91° C. and a reduced pressure of 8.0 hPa to 20 hPa, to obtain 3.8 g of (1S)-2-chloro-2-fluorocyclopropanecarboxylic acid ethyl ester (content: 86.2 weight %, net: 3.3 g, anti/syn ratio=58.4/41.6, optical purity of anti configuration=96.3% ee) in the form of a colorless oily substance.

Example 12

Distillation of (1S)-2-chloro-2-fluorocyclopropanecarboxylic acid ethyl ester

Reactions were repeatedly conducted under conditions that were almost the same as those in Example 7-1. The mixture containing (1S)-2-chloro-2-fluorocyclopropanecarboxylic acid ethyl ester obtained in each reaction was united, to obtain 2,331 g of a mixture containing (1S)-2-chloro-2-fluorocyclopropanecarboxylic acid ethyl ester (content: 22.7 weight %, net: 528 g, anti/syn ratio=62.8/37.2, optical purity of anti configuration=98.2% ee). After adding 30.9 g of 4 A molecular sieve, the mixture thus obtained was concentrated at a temperature of 39° C. to 42° C. and a reduced pressure of 47 hPa to 373 hPa until the weight thereof became 775 g (content: 64.2%, net: 498 g). Out of 775 g of the mixture, 385 g thereof was subjected to distillation at a temperature of 73° C. to 107° C. and a reduced pressure of 5.3 hPa to 13 hPa, to obtain 247 g of (1S)-2-chloro-2-fluorocyclopropanecarboxylic acid ethyl ester (content: 97.4 weight %, net: 241 g, anti/syn ratio=62.0/38.0, optical purity of anti configuration=98.2% ee) in the form of a colorless oily substance.

Example 13

(1S,2R)-2-Chloro-2-fluorocyclopropanecarboxylic acid

A 0.2 mol/L phosphoric acid buffer solution (1,812 g) containing 52.3 g of sodium dihydrogen phosphate and 1,760 g of water was placed in a 3,000-mL round-bottom separable flask at room temperature. A 10 weight % sodium hydroxide aqueous solution was added thereto to adjust its pH to 6.5. (1S)-2-Chloro-2-fluorocyclopropanecarboxylic acid ethyl ester obtained in Example 8 (224 g, content: 98.1 weight %, net: 220 g, 1.32 mol, anti/syn ratio=61.1/38.9, optical purity of anti configuration=98.2% ee) and 11.0 g of a hydrolase having an amino acid sequence represented by SEQ ID NO: 1 (product name: Lipase AH (produced by Amano Enzyme Inc., Lot. No. LAHG0150707R)) were subsequently supplied to the flask, and the resulting mixture was stirred at 35° C. for 50 hours. While stirring, the pH of the mixture was adjusted to 6.5 using a 10 weight % sodium hydroxide aqueous solution. After the reaction was completed, the pH of the reaction mixture was adjusted to 2.0 by adding 1,100 g of tert-butyl methyl ether and 35 weight % hydrochloric acid, followed by separation of the organic layer and the water layer. Thereafter, the water layer was subjected to extraction using 440 g of tert-butyl methyl ether, and the organic layer thus obtained was united with the organic layer obtained in the previous step. To the resulting organic layer, 11 g of Radiolight (registered trademark, produced by Showa Chemical Industry Co., Ltd.) was added, and the mixture was stirred at room temperature, followed by filtration using a glass filter to remove solid components. A slight amount of water layer generated during the filtration was removed, to obtain 1,806 g of organic layer containing (1S,2R)-2-chloro-2-fluorocyclopropanecarboxylic acid (content: 5.79 weight %, net: 104.5 g, yield: 57.1%, anti/syn ratio=98.6/1.4, optical purity of anti configuration=98.1% ee). The organic layer thus obtained was cooled to 5° C. While maintaining the temperature at 5° C. to 15° C., a 27 weight % sodium hydroxide aqueous solution (117 g, 0.787 mol) was added thereto dropwise to adjust the pH to 13. After adjusting the internal temperature to 20° C., (1S,2R)-2-chloro-2-fluorocyclopropanecarboxylic acid was extracted to the water layer in the form of sodium salt, to obtain 285 g of a water layer containing sodium (1S,2R)-2-chloro-2-fluorocyclopropanecarboxylate (the sodium (1S,2R)-2-chloro-2-fluorocyclopropanecarboxylate had the following properties: content: 41.4 weight %, net: 118 g, yield: 55.7%, and anti/syn ratio=98.1/1.9, and optical purity of anti configuration=98.1% ee).

Example 14

(1S,2R)-2-Chloro-2-fluorocyclopropanecarboxylic acid

A 0.2 mol/L phosphoric acid buffer solution (614.3 g) containing 14.3 g of sodium dihydrogen phosphate and 600 g of water was placed in a 2,000-mL round-bottom separable flask at room temperature. A 10 weight % sodium hydroxide aqueous solution was added thereto to adjust its pH to 6.5. (1S)-2-Chloro-2-fluorocyclopropanecarboxylic acid ethyl ester obtained in Example 10 (61.2 g, content: 97.4 weight %, net: 60.0 g, 0.360 mol, anti/syn ratio=62.4/37.6, optical purity of anti configuration=98.2% ee) and 3.0 g of a hydrolase having an amino acid sequence represented by SEQ ID NO: 1 (product name: Lipase AH (produced by Amano Enzyme Inc., Lot. No. LAHG0150707R)) were subsequently supplied to the flask, and the resulting mixture was stirred at 35° C. for 47 hours. While stirring, the pH of the mixture was adjusted to 6.5 using a 10 weight % sodium hydroxide aqueous solution. After the reaction was completed, the pH of the reaction mixture was adjusted to 2.3 by adding thereto 300 g of tert-butyl methyl ether and 35 weight % hydrochloric acid, followed by separation of the organic layer and the water layer. Thereafter, the water layer was subjected to extraction twice using 120 g of tert-butyl methyl ether, and the organic layer thus obtained was united with the organic layer obtained in the previous step. To the resulting organic layer, 6 g of Radiolight (registered trademark, produced by Showa Chemical Industry Co., Ltd.) was added. The mixture was stirred at room temperature and then filtered through a glass filter using the Radiolight (registered trademark, produced by Showa Chemical Industry Co., Ltd.) as a filter medium to remove solid components. A slight amount of water layer generated in the filtrate was removed, to obtain 539 g of an organic layer containing (1S,2R)-2-chloro-2-fluorocyclopropanecarboxylic acid (the (1S,2R)-2-chloro-2-fluorocyclopropanecarboxylic acid having the properties of content: 9.20 weight %, net: 29.9 g, yield: 61.2%, anti/syn ratio=98.6/1.4, and optical purity of anti configuration=98.1% ee).

Example 15

(1S,2R)-2-Chloro-2-fluorocyclopropanecarboxylic acid

Out of the total amount of a 0.2 mol/L phosphoric acid buffer solution containing 9.6 g of sodium dihydrogen phosphate and 390.4 g of water, 300 g thereof was placed in a 500-mL round-bottom separable flask at room temperature. A 28 weight % sodium hydroxide aqueous solution was added thereto to adjust its pH to 6.9. (1S)-2-Chloro-2-fluorocyclopropanecarboxylic acid ethyl ester obtained in Example 11 (30.0 g, content: 100 weight %, net: 30.0 g, 0.180 mol, anti/syn ratio=61.7/38.3, optical purity of anti configuration=98.2% ee) and 6.0 g of a hydrolase having an amino acid sequence represented by SEQ ID NO: 2 (product name: Lipase PS (produced by Amano Enzyme Inc., Lot. No. LPSAP11522)) were subsequently supplied to the flask, and the resulting mixture was stirred at 35° C. for 48 hours. While stirring, the pH of the mixture was adjusted to 6.9 using a 4 weight % sodium hydroxide aqueous solution. After the reaction was completed, the pH of the reaction mixture was adjusted to 2.0 by adding 150 g of tert-butyl methyl ether and 4 weight % hydrochloric acid, followed by separation of the organic layer and the water layer. Thereafter, the water layer was subjected to extraction twice using 150 g of tert-butyl methyl ether, and the organic layer thus obtained was united with the organic layer obtained in the previous step. To the resulting organic layer, 9 g of Radiolight (registered trademark, produced by Showa Chemical Industry Co., Ltd.) was added. The mixture was stirred at room temperature and then filtered through a glass filter using the Radiolight (registered trademark, produced by Showa Chemical Industry Co., Ltd.) as a filter medium to remove solid components. A slight amount of water layer generated in the filtrate was removed, to obtain 480 g of an organic layer containing (1S,2R)-2-chloro-2-fluorocyclopropanecarboxylic acid (the (1S,2R)-2-chloro-2-fluorocyclopropanecarboxylic acid having the properties of content: 3.13 weight %, net: 15.0 g, yield: 60.1%, anti/syn ratio=95.5/4.5, and optical purity of anti configuration=98.0% ee).

Example 16

(1S,2R)-2-Chloro-2-fluorocyclopropanecarboxylic acid

Out of the total amount of a 0.2 mol/L phosphoric acid buffer solution containing 2.4 g of sodium dihydrogen phosphate and 100 g of water, 30 g thereof was placed in a 100-mL reaction vessel at room temperature. A 28 weight % sodium hydroxide aqueous solution was added thereto to adjust its pH to 6.5. (1S)-2-Chloro-2-fluorocyclopropanecarboxylic acid ethyl ester obtained in Example 9 (1.02 g, content: 98.4 weight %, net: 1.00 g, 6.00 mol, anti/syn ratio=62.5/37.5, optical purity of anti configuration=98.3% ee) and 50 g of a hydrolase having an amino acid sequence represented by SEQ ID NO: 1 (product name: Lipase AH (produced by Amano Enzyme Inc., Lot. No. LAHG0150707R)) were subsequently supplied to the reaction vessel, and the resulting mixture was stirred at 30° C. for 48 hours. While stirring, the pH of the mixture was adjusted to 6.5 to 7.0 using a 4 weight % sodium hydroxide aqueous solution. After the reaction was completed, the pH of the reaction mixture was adjusted to 2.0 by adding 20 g of tert-butyl methyl ether and 5 weight % hydrochloric acid, followed by separation of the organic layer and the water layer. Thereafter, the water layer was subjected to extraction using 20 g of tert-butyl methyl ether, and the organic layer thus obtained was united with the organic layer obtained in the previous step. To the resulting organic layer, a slight amount of Radiolight (registered trademark, produced by Showa Chemical Industry Co., Ltd.) was added. The mixture was stirred at room temperature and then filtered through a glass filter using the Radiolight (registered trademark, produced by Showa Chemical Industry Co., Ltd.) as a filter medium to remove solid components. A slight amount of water layer generated in the filtrate was removed, to obtain 49.2 g of an organic layer containing (1S,2R)-2-chloro-2-fluorocyclopropanecarboxylic acid (the (1S,2R)-2-chloro-2-fluorocyclopropanecarboxylic acid having the properties of content: 0.87 weight %, net: 0.428 g, yield: 51.5%, anti/syn ratio=99.7/0.3, and optical purity of anti configuration=98.0% ee).

Example 17

(1S,2R)-2-Chloro-2-fluorocyclopropanecarboxylic acid

A 0.75 mol/L sodium hydrogen carbonate buffer solution (127.6 g) containing 7.60 g of sodium hydrogen carbonate and 120 g of water was placed in a 300-mL round-bottom separable flask at room temperature. (1S)-2-Chloro-2-fluorocyclopropanecarboxylic acid ethyl ester obtained in Example 9 (15.2 g, content: 98.4 weight %, net: 15.0 g, 90.0 mol, anti/syn ratio=62.5/37.5, optical purity of anti configuration=98.3% ee) and 750 mg of a hydrolase having an amino acid sequence represented by SEQ ID NO: 1 (product name: Lipase AH (produced by Amano Enzyme Inc., Lot. No. LAHG0150707R)) were subsequently supplied to the flask, and the resulting mixture was stirred at 35° C. for 48 hours. After the reaction was completed, the pH of the reaction mixture was adjusted to 2.0 by adding 30 g of tert-butyl methyl ether and 35 weight % hydrochloric acid, followed by separation of the organic layer and the water layer. Thereafter, the water layer was subjected to extraction using 30 g of tert-butyl methyl ether, and the organic layer thus obtained was united with the organic layer obtained in the previous step. To the resulting organic layer, 0.8 g of Radiolight (registered trademark, produced by Showa Chemical Industry Co., Ltd.) was added. The mixture was stirred at room temperature and then filtered through a glass filter to remove solid components. A slight amount of water layer generated in the filtrate was removed, to obtain 59.4 g of an organic layer containing (1S,2R)-2-chloro-2-fluorocyclopropanecarboxylic acid (the (1S,2R)-2-chloro-2-fluorocyclopropanecarboxylic acid having the properties of content: 12.7 weight %, net: 7.56 g, yield: 60.6%, anti/syn ratio=98.2/1.8, and optical purity of anti configuration=98.2% ee).

Example 17-1

(1S,2R)-2-Chloro-2-fluorocyclopropanecarboxylic acid

A 0.97 mol/L sodium hydrogen carbonate solution (522.4 g) containing 42.4 g of sodium hydrogen carbonate and 480 g of water was placed in a 1,000-mL round-bottom separable flask at room temperature. (1S)-2-Chloro-2-fluorocyclopropanecarboxylic acid ethyl ester obtained according to Example 12-1 (123 g, content: 97.3 weight %, net: 120 g, 0.720 mol, anti/syn ratio=62.2/37.8, optical purity of anti configuration=98.2% ee) and 8.40 g of a hydrolase having an amino acid sequence represented by SEQ ID NO: 1 (product name: Lipase AH (produced by Amano Enzyme Inc., Lot. No. LAHG0951102R)) were subsequently supplied to the flask, and the resulting mixture was stirred at 35° C. for 62 hours. After the reaction was completed, the pH of the reaction mixture was adjusted to 2.0 by adding 240 g of tert-butyl methyl ether and 35 weight % hydrochloric acid, followed by separation of the organic layer and the water layer. Thereafter, the water layer was subjected to extraction using 60 g of tert-butyl methyl ether, and the organic layer thus obtained was united with the organic layer obtained in the previous step. To the resulting organic layer, 6.0 g of Radiolight (registered trademark, produced by Showa Chemical Industry Co., Ltd.) was added. The mixture was stirred at room temperature and then filtered through a glass filter to remove solid components. A slight amount of water layer generated in the filtrate was removed, to obtain 400 g of an organic layer containing (1S,2R)-2-chloro-2-fluorocyclopropanecarboxylic acid (the (1S,2R)-2-chloro-2-fluorocyclopropanecarboxylic acid having the properties of content: 15.1 weight %, net: 60.4 g, yield: 60.4%, anti/syn ratio=98.8/1.2, and optical purity of anti configuration=98.1% ee). The organic layer thus obtained was cooled to 5° C. While maintaining the temperature at 5° C. to 15° C., a 26 weight % sodium hydroxide aqueous solution (55.4 g, 0.360 mol) and a 10 weight % sodium hydroxide aqueous solution (35.4 g) were sequentially added dropwise to adjust the pH to 13. After adjusting the internal temperature to 20° C., (1S,2R)-2-chloro-2-fluorocyclopropanecarboxylic acid was extracted to the water layer in the form of a sodium salt. A 35% hydrochloric acid solution was added to adjust its pH to 7, to obtain 185 g of an aqueous solution containing sodium (1S,2R)-2-chloro-2-fluorocyclopropanecarboxylate (the sodium (1S,2R)-2-chloro-2-fluorocyclopropanecarboxylate having the properties of content: 36.0 weight %, net: 66.6 g, yield: 57.4%, anti/syn ratio=98.8/1.2, and optical purity of anti configuration=98.1% ee).

Example 17-2

(1S,2R)-2-Chloro-2-fluorocyclopropanecarboxylic acid

A 0.97 mol/L sodium hydrogen carbonate buffer solution (108.8 g) containing 8.83 g of sodium hydrogen carbonate and 100 g of water was placed in a 200-mL round-bottom separable flask at room temperature. (1S)-2-Chloro-2-fluorocyclopropanecarboxylic acid ethyl ester obtained according to Example 12-1 (25.7 g, content: 97.3 weight %, net: 25.0 g, 0.150 mol, anti/syn ratio=62.2/37.8, optical purity of anti configuration=98.2% ee) and 1.75 g of a hydrolase having an amino acid sequence represented by SEQ ID NO: 1 (product name: Lipase AH (produced by Amano Enzyme Inc., Lot. No. LAHH0250804R)) were subsequently supplied to the flask, and the resulting mixture was stirred at 35° C. for 40 hours. After the reaction was completed, the pH of the reaction mixture was adjusted to 2.0 by adding 50.0 g of tert-butyl methyl ether and 35 weight % hydrochloric acid, followed by separation of the organic layer and the water layer. Thereafter, the water layer was subjected to extraction using 12.5 g of tert-butyl methyl ether, and the organic layer thus obtained was united with the organic layer obtained in the previous step. To the resulting organic layer, 1.3 g of Radiolight (registered trademark, produced by Showa Chemical Industry Co., Ltd.) was added. The mixture was stirred at room temperature and then filtered through a glass filter to remove solid components. A slight amount of water layer generated in the filtrate was removed, to obtain 82.6 g of organic layer containing (1S,2R)-2-chloro-2-fluorocyclopropanecarboxylic acid (the (1S,2R)-2-chloro-2-fluorocyclopropanecarboxylic acid having the properties of content: 14.6 weight %, net: 12.1 g, yield: 57.9%, anti/syn ratio=98.9/1.1, and optical purity of anti configuration=98.1% ee).

Example 18

(1S,2S)-2-fluorocyclopropanecarboxylic acid

While stirring an aqueous solution of the sodium (1S,2R)-2-chloro-2-fluorocyclopropanecarboxylate obtained in Example 13 (282 g, content: 41.4 weight %, net: 117 g, 0.728 mol, anti/syn ratio=98.1/1.9, optical purity of anti configuration=98.1% ee) at an ordinary temperature, a nickel-aluminum alloy (30.7 g, nickel content: 49.7 weight %, aluminum content: 50.2 weight %, aluminum net: 15.4 g, 0.571 mol) was added to the solution. While keeping the internal temperature of the mixture at 25° C. to 30° C., ethylenediamine (2.19 g, 0.036 mol) and a 27 weight% sodium hydroxide aqueous solution (5.40 g, 0.036 mol) were added to the mixture over a period of 30 minutes. While keeping the internal temperature of the resulting mixture at 29° C. to 42° C., ethylenediamine (43.8 g, 0.729 mol) and a 27 weight % sodium hydroxide aqueous solution (113 g, 0.765 mol) were added thereto over a period of 3.5 hours. Subsequently, the internal temperature of the mixture was raised to 50° C. over a period of 1 hour, followed by stirring for 3 hours at the same temperature.

Water (73 g) was added thereto and the resulting mixture was stirred at the same temperature for 15 minutes. After stirring, the catalyst derived from the nickel-aluminum alloy was removed from the mixture using a filter that had been kept at 65±5° C. The catalyst remaining on the filter was washed with 36 g of 70° C. water three times, to obtain 550 g of a solution containing sodium (1S,2S)-2-fluorocyclopropanecarboxylate (content: 15.9 weight %, net: 87.6 g, yield: 95.4%, cis/trans ratio=98.1/1.9, cis isomer optical purity=98.0% ee). The cis/trans ratio was measured by high-performance liquid chromatography.

To the resulting solution, 281 g of 35 weight % hydrochloric acid was added and its pH was adjusted to 2.0. The mixture thus obtained was subjected to extraction using 110 g of tert-butyl methyl ether 6 times. The organic layers obtained were united. While conducting the extraction, the pH of the water layer was adjusted to 2.0 using 35 weight % hydrochloric acid. The total amount of the obtained organic layer (728 g) was concentrated under reduced pressure, to obtain 114 g of a mixture containing (1S,2S)-2-fluorocyclopropanecarboxylic acid (content: 63.3 weight %, net: 70.5 g, cis/trans ratio=98.0/2.0). After adding 102 g of toluene to the mixture, the resulting mixture was concentrated under reduced pressure, to obtain 111 g of a mixture containing (1S,2S)-2-fluorocyclopropanecarboxylic acid. Toluene (102 g) was added to the mixture, making the total amount of the mixture 213 g (content: 34.0 weight %, net: 72.2 g, cis/trans ratio=98.3/1.7). The cis/trans ratio was measured by high-performance liquid chromatography.

Out of the total amount of the resulting mixture containing (1S,2S)-2-fluorocyclopropanecarboxylic acid, 21.7 g thereof (net: 7.38 g) was concentrated under reduced pressure until the amount became 14.4 g. Toluene was added to the mixture, making the total amount 18.1 g. The internal temperature of the resulting mixture was adjusted to 35° C., to obtain a homogeneous solution. The solution was gradually cooled while stirring, and a seed crystal of (1S,2S)-2-fluorocyclopropanecarboxylic acid was added thereto when the temperature thereof became 26° C. The mixture was kept at 25° C. for 1 hour while stirring and then cooled by 5° C. every hour. Crystals gradually precipitated in the mixture while cooling. When the temperature of the mixture reached 0° C., the mixture was kept at 0° C. for 15 hours. n-Heptane (7.8 g) was added to the mixture dropwise over a period of 1 hour while the temperature was maintained at 0° C. After stirring for 2 hours, 7.8 g of n-heptane was further added to the mixture dropwise over a period of 1 hour, followed by stirring for 3.5 hours. Thereafter, 17.5 g of n-heptane was added to the mixture dropwise over a period of 2 hours, followed by stirring for 14 hours. Then 17.5 g of n-heptane was added to the mixture dropwise over a period of 2 hours, followed by stirring for 45 minutes.

After adding 17.5 g of n-heptane to the mixture dropwise over a period of 2 hours and stirring the mixture for 30 minutes, the precipitated crystals were subjected to filtration. The crystals thus obtained were dried by passing a nitrogen gas thereover, to obtain 6.03 g of white crystals of (1S,2S)-2-fluorocyclopropanecarboxylic acid (content: 99.9 weight %, crystallization yield: 81.7%, cis/trans ratio=99.9/0.1, cis isomer optical purity=99.8% ee or more). The cis/trans ratio was measured by gas chromatography.

Example 18-1

(1S,2S)-2-fluorocyclopropanecarboxylic acid
(Development Reduction)

Wile stirring 77.9 g of an aqueous solution of the sodium (1S,2R)-2-chloro-2-fluorocyclopropanecarboxylate obtained in Example 17-1 (content: 36.0 weight %, net: 28.0 g, 0.174 mol, anti/syn ratio=98.8/1.2, optical purity of anti configuration=98.1% ee) at an ordinary temperature, 7.35 g of a nickel-aluminum alloy (nickel content: 49.7 weight %, aluminum content: 50.2 weight %, aluminum net: 3.67 g, 0.136 mol) was added to the solution. While maintaining the internal temperature of the mixture at 10° C. to 20° C., 1.05 g of ethylenediamine (0.017 mol) and 2.68 g of a 26 weight % sodium hydroxide aqueous solution (0.017 mol) were added to the mixture over a period of 2 hours. The mixture was stirred at the same temperature for 1 hour. While keeping the internal temperature of the mixture at 35° C. to 45° C., 10.0 g of ethylenediamine (0.166 mol) and 26.8 g of a 26 weight % sodium hydroxide aqueous solution (0.174 mol) were added to the mixture over a period of 16 hours. The resulting mixture was stirred for 1 hour while maintaining the internal temperature at 40° C. After adding 17 g of water, the mixture was heated to 65° C. and then stirred for 15 minutes at the same temperature. After stirring, the catalyst derived from the nickel-aluminum alloy was removed from the mixture using a filter kept at 65±5° C. By washing the catalyst remaining on the filter with 8.7 g of 70° C. hot water 3 times, 137 g of solution containing sodium (1S,2S)-2-fluorocyclopropanecarboxylate (content: 14.8 weight %, net: 20.3 g, yield: 92.2%, cis/trans ratio=97.2/2.8, cis isomer optical purity=97.8% ee) was obtained. The cis/trans ratio was measured by high-performance liquid chromatography.

Example 18-2

(1S,2S)-2-Fluorocyclopropanecarboxylic acid
(crystallization)

To 283 g of a solution containing sodium (1S,2S)-2-fluorocyclopropanecarboxylate obtained according to the process of Example 18-1 (content: 12.1 weight %, net: 34.2 g, cis/trans ratio=97.3/2.7, cis isomer optical purity=98.0% ee), 97 g of 35 weight % hydrochloric acid was added, followed by adjustment of its pH to 1 or less. The resulting mixture was subjected to extraction three times using 102 g of tert-butyl methyl ether, and the resulting organic layers were united. The total amount (304 g) of the organic layer obtained was concentrated under reduced pressure, to obtain 67.2 g of a mixture containing (1S,2S)-2-fluorocyclopropanecarboxylic acid (content: 42.1 weight %, net: 28.3 g, cis/trans ratio=96.9/3.1). After adding 44 g of toluene to the mixture, the resulting mixture was concentrated under reduced pressure. Further, 44 g of toluene was added to the mixture and concentrated under reduced pressure again, to obtain 45.4 g of a mixture containing (1S,2S)-2-fluorocyclopropanecarboxylic acid (content: 58.6 weight %, net: 26.6 g).

Toluene was added to 43.1 g of the total amount of the resulting mixture containing (1S,2S)-2-fluorocyclopropanecarboxylic acid (net: 25.3 g), making the total amount 50.5 g. A seed crystal of (1S,2S)-2-fluorocyclopropanecarboxylic acid was added to the resulting solution while stirring at 30° C. The resulting mixture was kept at 28° C. for 1 hour while stirring and then cooled by 5° C. every hour. Crystals gradually precipitated in the mixture while cooling. When the temperature of the mixture reached −5° C., the mixture was kept at the same temperature for 5 hours. After adding 152 g of n-heptane to the mixture dropwise over a period of 3 hours while keeping the temperature at −5° C., the mixture was stirred for 1 hour. The precipitated crystals were subjected to filtration and then washed with a mixed solvent of 38 g of n-heptane and 6 g of toluene having a temperature of −5° C. The crystals thus obtained were dried by being passed through a nitrogen gas, to obtain 22.8 g of white crystals of (1S,2S)-2-fluorocyclopropanecarboxylic acid (content: 100 weight %, crystallization yield: 90.1%, cis/trans ratio=100.0/0.0, cis isomer optical purity=99.4% ee or more). The cis/trans ratio was measured by gas chromatography.

Example 19

(1S,2S)-2-Fluorocyclopropanecarboxylic acid

A 10 weight % sodium hydroxide aqueous solution (2.88 g, 7.2 mmol) was added to 1.11 g of (1S,2R)-2-chloro-2-fluorocyclopropanecarboxylic acid (content: 93.7 weight %, net: 1.04 g, 7.5 mmol, anti/syn ratio=96.1/3.9, optical purity of anti configuration=97.7% ee) while stirring at 0 to 15° C. to prepare a sodium (1S,2R)-2-chloro-2-fluorocyclopropanecarboxylate aqueous solution. After adjusting the inner temperature of a 50-mL autoclave to 0° C. to 10° C., 1.2 mL of an activated sponge nickel (produced by Kawaken Fine Chemicals Co., Ltd., NDHT-90) precipitate (corresponding to nickel net of 1.0 g), ethylenediamine (1.30 g, 0.0216 mol) and water (2.20 g) were supplied to the autoclave while stirring. While maintaining the internal temperature at 10° C. to 30° C., the total amount of the sodium (1S,2R)-2-chloro-2-fluorocyclopropanecarboxylate aqueous solution prepared in advance was added to the resulting mixture dropwise. After sealing the autoclave, hydrogen was enclosed therein to make the internal pressure of the autoclave 0.8 MPa. The resulting mixture was heated to 35° C. and stirred for 6 hours. After the reaction was completed, a catalyst derived from the activated sponge nickel was removed by filtration from the reaction mixture using Radiolight (registered trademark, produced by Showa Chemical Industry Co., Ltd.). The residue after filtration was washed using 10 g of water and 10 g of ethanol in sequence. The resulting wash liquid and the filtrate obtained in advance were united. The resulting mixture was concentrated under reduced pressure until the total amount thereof became 18 g. The pH of the mixture was adjusted to 2.0 using 35 weight % hydrochloric acid. The resulting solution was subjected to extraction twice using 10 g of tert-butyl methyl ether, to obtain 20.7 g of an organic layer containing (1S,2S)-2-fluorocyclopropanecarboxylic acid (content: 2.29 weight %, net:

0.47 g, yield: 60.5%, cis/trans ratio=98.3/1.7, cis isomer optical purity=97.9% ee). The cis/trans ratio was obtained by high-performance liquid chromatography. Analysis of the water layer revealed that the yield of the (1S,2S)-2-fluorocyclopropanecarboxylic acid contained in the water layer was 4.1%. Therefore, the reaction yield was 64.6%.

Reference Example 1

(1R)-2-Chloro-2-fluorocyclopropanecarboxylic acid ethyl ester

An [(R)-N-(5-nitrosalicylidene)-2-amino-1,1-di(5-tert-butyl-2-butoxyphenyl)-1-propanol] copper complex (278 mg, 0.40 mmol) and 45.6 g of dichloromethane were supplied to a 260-mL autoclave under a nitrogen atmosphere at an ordinary temperature. The reaction vessel was cooled to 0° C. while stirring the resulting mixture. After sealing the reaction vessel, 6.4 g of 1-chloro-1-fluoroethylene (0.080 mol) was supplied thereto under pressure, and the internal temperature was adjusted to 5±2° C. While maintaining the internal temperature at 5±2° C., a solution prepared by dissolving 9.60 g of ethyl diazoacetate (content: 95.3 weight %, net: 9.13 g, 0.080 mol) produced according to the method of Production Example 3 in 45.6 g of dichloromethane was added to the mixture dropwise over a period of 5 hours, and the resulting mixture was then stirred at the same temperature for 1 hour. After resetting the pressure, the temperature was increased and the atmosphere was then replaced with a nitrogen atmosphere. The reaction mixture thus prepared was washed with 2 g of a 0.5 mol/L ethylenediaminetetraacetic acid aqueous solution to conduct liquid-liquid separation, to obtain a mixture containing (1R)-2-chloro-2-fluorocyclopropanecarboxylic acid ethyl ester. The resulting mixture had the following properties: yield=8.5% (relative to ethyl diazoacetate), anti/syn ratio=47/53, optical purity of anti configuration=92.7% ee, optical purity of syn configuration=94.7% ee.

Comparative Example 1

(1S,2R)-2-chloro-2-fluorocyclopropanecarboxylic acid

After dissolving 9.6 g of sodium dihydrogen phosphate in 390.4 g of water, a 28 weight % sodium hydroxide aqueous solution was added to the mixture to adjust the pH to 7.0, to prepare 400 g of a 0.2 mol/L phosphoric acid buffer solution. At room temperature, 2.5 mL of the resulting phosphoric acid buffer solution, 25 mg of (1S)-2-chloro-2-fluorocyclopropanecarboxylic acid ethyl ester obtained in Example 12 (content: 86.2 weight %, net: 21.6 mg, 0.129 mmol, anti/syn ratio=58.4/41.6, optical purity of anti configuration=96.3% ee), and 5 mg of a hydrolase (product name: Protease A "Amano" (produced by Amano Enzyme Inc., Aspergillus oryzae)) were supplied to a 20-mL sample tube. The mixture thus obtained was stirred at 35° C. for 21 hours. After the reaction was completed, 3 g of tert-butyl methyl ether and 1.0 mL of 5 weight % sodium hydrogen carbonate were added to the reaction mixture. After stirring, the solid components in the reaction mixture were removed using a GL chromato disk (Produced by GL Sciences, Inc.). The organic layer was separated from the water layer, to obtain an organic layer A containing (1S,2R)-2-chloro-2-fluorocyclopropanecarboxylic acid ethyl ester. The water layer was subjected to extraction using 2 g of tert-butyl methyl ether and 0.8 mL of 5 weight % hydrochloric acid. The resulting organic layer was separated from the water layer, to obtain an organic layer B containing (1S,2R)-2-chloro-2-fluorocyclopropanecarboxylic acid (yield: 53.6%, anti/syn ratio=56.5/43.5, optical purity of anti configuration=85.8% ee).

Comparative Example 2

The same procedure as that in Comparative Example 1 was conducted except that Protease P "Amano" 3 (produced by Amano Enzyme Inc., Aspergillus melleus)) was used as the hydrolase, to obtain an organic layer B containing (1S,2R)-2-chloro-2-fluorocyclopropanecarboxylic acid (yield: 12.8%, anti/syn ratio=50.9/49.1, optical purity of anti configuration=81.0% ee).

Comparative Example 3

The same procedure as that in Comparative Example 1 was conducted except that Protease S "Amano" (produced by Amano Enzyme Inc., Bacillus stearothermophilus) was used as the hydrolase, to obtain an organic layer B containing (1S,2R)-2-chloro-2-fluorocyclopropanecarboxylic acid (yield: 58.8%, anti/syn ratio=56.3/43.7, optical purity of anti configuration=56.8% ee or more (detection limit)).

Comparative Example 4

The same procedure as that in Comparative Example 1 was conducted except that Papain W-40 (produced by Amano Enzyme Inc., Caricapapaya) was used as the hydrolase, to obtain an organic layer B containing (1S,2R)-2-chloro-2-fluorocyclopropanecarboxylic acid (yield: 77.9%, anti/syn ratio=57.8/42.2, optical purity of anti configuration=58.5% ee or more (detection limit)).

In the Comparative Examples above, the yield, anti/syn ratio, and optical purity of (1S,2R)-2-chloro-2-fluorocyclopropanecarboxylic acid were obtained by the methods described below.

(1S,2R)-2-Chloro-2-fluorocyclopropanecarboxylic acid

Anti/syn ratio: Gas chromatography analysis
Column: DB-WAX
0.53 mm×30 m, membrane thickness of 1.0 μm (Produced by Agilent Technologies, Inc.)
Method: Analysis was conducted after derivatizing (1S,2R)-2-chloro-2-fluorocyclopropanecarboxylic acid to methyl ester using trimethylsilyldiazomethane.
Optical purity: Gas chromatography analysis
Column: InertCap (registered trademark) CHIRAMIX
0.25 mm×30 m, membrane thickness of 0.25 μm (Produced by GL Sciences, Inc.)
Method: Analysis was conducted after derivatizing (1S,2R)-2-chloro-2-fluorocyclopropanecarboxylic acid to methyl ester using trimethylsilyldiazomethane.
Industrial Applicability
(1S,2R)-2-Chloro-2-fluorocyclopropanecarboxylic acid and (1S,2S)-2-fluorocyclopropanecarboxylic acid are useful as intermediates for medicines and agricultural chemicals (for example, Japanese Unexamined Patent Publication No. 1990-231475, and Japanese Unexamined Patent Publication No. 2005-15468). The present invention is useful as a method for industrially manufacturing such compounds.
[Sequence List]
PCT (1S,2R)-2-20090707 144522 3.txt

The invention claimed is:

1. A method for producing (1S,2R)-2-chloro-2-fluorocyclopropanecarboxylic acid comprising hydrolyzing a (1S)-2-chloro-2-fluorocyclopropanecarboxylic acid ester using an esterase obtained from *Burkholderia cepacia*.

2. The production method according to claim 1, wherein the method comprises reacting 1-chloro-1-fluoroethylene with diazoacetic acid ester in the presence of an asymmetric complex to obtain (1S)-2-chloro-2-fluorocyclopropanecarboxylic acid ester, and hydrolyzing the (1S)-2-chloro-2-fluorocyclopropanecarboxylic acid ester using an esterase obtained from *Burkholderia cepacia*.

3. The production method according to claim 2, wherein the asymmetric complex is an asymmetric copper complex obtained by contacting a copper compound with an optically active ligand.

4. The production method according to claim 3, wherein the optically active ligand is an optically active bisoxazoline compound shown in Formula (1):

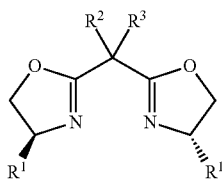

(1)

wherein R¹ represents a $C_{1-4}$ alkyl group, a phenyl group that may be substituted, an aralkyl group that may be substituted, 1-naphthyl group, or 2-naphthyl group; and R² and R³ are the same or different and each represents a hydrogen atom or a $C_{1-3}$ alkyl group.

5. The production method according to claim 3, wherein the optically active ligand is 2,2-bis[2[(4S)-tert-butyloxazoline]]propane.

6. The production method according to claim 1, wherein the esterase derived from *Burkholderia cepacia* is an esterase having an amino acid sequence shown in SEQ ID NO: 1 or 2.

7. The production method according to claim 1, wherein the esterase derived from *Burkholderia cepacia* is an esterase having an amino acid sequence shown in SEQ ID NO: 1.

8. A method for producing (1S,2S)-2-fluorocyclopropanecarboxylic acid comprising:
   producing (1S,2R)-2-chloro-2-fluorocyclopropanecarboxylic acid by the production method according to any one of claims 1 to 7; and
   reducing the (1S,2R)-2-chloro-2-fluorocyclopropanecarboxylic acid.

9. The production method according to claim 8, wherein the reduction is conducted by allowing a base to react with a nickel-aluminum alloy in the presence of (1S,2R)-2-chloro-2-fluorocyclopropanecarboxylic acid.

* * * * *

SEQUENCE LISTING

<160> NUMBER OF SEQ ID NOS: 2

<210> SEQ ID NO 1
<211> LENGTH: 320
<212> TYPE: PRT
<213> ORGANISM: Burkholderia cepacia

<400> SEQUENCE: 1

```
Ala Asp Asn Tyr Ala Ala Thr Arg Tyr Pro Ile Ile Leu Val His Gly
1               5                   10                  15

Leu Thr Gly Thr Asp Lys Tyr Ala Gly Val Leu Asp Tyr Trp Tyr Gly
            20                  25                  30

Ile Gln Glu Asn Leu Gln Gln His Gly Ala Thr Val Tyr Val Ala Asn
        35                  40                  45

Leu Ser Gly Phe Gln Ser Asp Asp Gly Pro Asn Gly Arg Gly Glu Gln
    50                  55                  60

Leu Leu Ala Tyr Val Lys Thr Val Leu Ala Ala Thr Gly Ala Thr Lys
65                  70                  75                  80

Val Asn Leu Val Gly His Ser Gln Gly Gly Leu Thr Ser Arg Tyr Val
                85                  90                  95

Ala Ala Val Ala Pro Asp Leu Val Ala Ser Val Thr Thr Ile Gly Thr
            100                 105                 110

Pro His Arg Gly Ser Glu Phe Ala Asp Phe Val Gln Gly Val Leu Ala
        115                 120                 125

Tyr Asp Pro Thr Gly Leu Ser Ser Thr Val Ile Ala Ala Phe Val Asn
    130                 135                 140

Val Phe Gly Ile Leu Thr Ser Ser Ser His Asn Thr Asn Gln Asp Ala
145                 150                 155                 160

Leu Ala Ala Leu Lys Thr Leu Thr Thr Ala Gln Ala Ala Thr Tyr Asn
                165                 170                 175

Gln Asn Tyr Pro Ser Ala Gly Leu Gly Ala Ser Gly Ser Cys Gln Thr
            180                 185                 190

Gly Ala Pro Thr Glu Thr Val Gly Gly Asn Thr His Leu Leu Tyr Ser
        195                 200                 205

Trp Ala Gly Thr Ala Ile Gln Pro Thr Phe Ser Val Leu Gly Val Thr
    210                 215                 220

Gly Ala Thr Asp Thr Ser Thr Ile Pro Leu Val Asp Pro Ala Asn Val
225                 230                 235                 240

Leu Asp Leu Ser Thr Leu Ala Leu Leu Gly Thr Gly Thr Val Met Ile
                245                 250                 255

Asn Arg Ala Ser Gly Gln Asn Asp Gly Leu Val Ser Lys Cys Ser Ala
            260                 265                 270

Leu Tyr Gly Lys Val Leu Ser Thr Ser Tyr Lys Trp Asn His Ile Asp
        275                 280                 285

Glu Ile Asn Gln Leu Leu Gly Val Arg Gly Ala Tyr Ala Glu Asp Pro
    290                 295                 300

Val Ala Val Ile Arg Thr His Ala Asn Arg Leu Lys Leu Ala Gly Val
305                 310                 315                 320
```

<210> SEQ ID NO 2
<211> LENGTH: 320
<212> TYPE: PRT
<213> ORGANISM: Burkholderia cepacia -continued

```
<400> SEQUENCE: 2

Ala Asp Asn Tyr Ala Ala Thr Arg Tyr Pro Ile Ile Leu Val His Gly
1               5                   10                  15

Leu Thr Gly Thr Asp Lys Tyr Ala Gly Val Leu Glu Tyr Trp Tyr Gly
            20                  25                  30

Ile Gln Glu Asp Leu Gln Gln Arg Gly Ala Thr Val Tyr Val Ala Asn
        35                  40                  45

Leu Ser Gly Phe Gln Ser Asp Asp Gly Pro Asn Gly Arg Gly Glu Gln
    50                  55                  60

Leu Leu Ala Tyr Val Lys Thr Val Leu Ala Ala Thr Gly Ala Thr Lys
65                  70                  75                  80

Val Asn Leu Val Gly His Ser Gln Gly Gly Leu Thr Ser Arg Tyr Val
                85                  90                  95

Ala Ala Val Ala Pro Asp Leu Val Ala Ser Val Thr Thr Ile Gly Thr
                100                 105                 110

Pro His Arg Gly Ser Glu Phe Ala Asp Phe Val Gln Gly Val Leu Ala
            115                 120                 125

Tyr Asp Pro Thr Gly Leu Ser Ser Thr Val Ile Ala Ala Phe Val Asn
    130                 135                 140

Val Phe Gly Ile Leu Thr Ser Ser Ser Asn Asn Thr Asn Gln Asp Ala
145                 150                 155                 160

Leu Ala Ala Leu Lys Thr Leu Thr Thr Ala Gln Ala Ala Thr Tyr Asn
                165                 170                 175

Gln Asn Tyr Pro Ser Ala Gly Leu Gly Ala Pro Gly Ser Cys Gln Thr
            180                 185                 190

Gly Ala Pro Thr Glu Thr Val Gly Gly Asn Thr His Leu Leu Tyr Ser
        195                 200                 205

Trp Ala Gly Thr Ala Ile Gln Pro Thr Ile Ser Val Phe Gly Val Thr
    210                 215                 220

Gly Ala Thr Asp Thr Ser Thr Ile Pro Leu Val Asp Pro Ala Asn Ala
225                 230                 235                 240

Leu Asp Pro Ser Thr Leu Ala Leu Phe Gly Thr Gly Thr Val Met Val
                245                 250                 255

Asn Arg Gly Ser Gly Gln Asn Asp Gly Val Val Ser Lys Cys Ser Ala
            260                 265                 270

Leu Tyr Gly Gln Val Leu Ser Thr Ser Tyr Lys Trp Asn His Leu Asp
        275                 280                 285

Glu Ile Asn Gln Leu Leu Gly Val Arg Gly Ala Asn Ala Glu Asp Pro
    290                 295                 300

Val Ala Val Ile Arg Thr His Ala Asn Arg Leu Lys Leu Ala Gly Val
305                 310                 315                 320
```